(12) United States Patent
Cotter et al.

(10) Patent No.: US 10,687,840 B1
(45) Date of Patent: Jun. 23, 2020

(54) ULTRASONIC TRANSDUCER TISSUE SELECTIVITY

(71) Applicant: Integra LifeSciences NR Ireland Limited, Dublin (IE)

(72) Inventors: Daniel J. Cotter, North Easton, MA (US); Prakash Manandhar, Lawrence, MA (US); Nicholas Allen, Bedford, MA (US); Saurav V. Gupta, Medway, MA (US)

(73) Assignee: Integra LifeSciences NR Ireland Limited, Dublin (IE)

( * ) Notice: Subject to any disclaimer, the term of this patent is extended or adjusted under 35 U.S.C. 154(b) by 320 days.

(21) Appl. No.: 15/816,666

(22) Filed: Nov. 17, 2017

Related U.S. Application Data

(60) Provisional application No. 62/423,407, filed on Nov. 17, 2016.

(51) Int. Cl.
*A61B 17/32* (2006.01)
*B06B 1/02* (2006.01)
(Continued)

(52) U.S. Cl.
CPC .... *A61B 17/320068* (2013.01); *B06B 1/0215* (2013.01); *B06B 1/0618* (2013.01);
(Continued)

(58) Field of Classification Search
CPC .......... A61B 17/320068; A61B 2017/320094; A61B 2017/320095; A61B 17/320092;
(Continued)

(56) References Cited

U.S. PATENT DOCUMENTS 4,063,557 A 12/1977 Wuchinich et al.
4,223,676 A 9/1980 Wuchinich et al.
(Continued)

FOREIGN PATENT DOCUMENTS

EP 1607075 12/2005
JP H0194841 A 4/1989
(Continued)

OTHER PUBLICATIONS

International Search Report and Written Opinion for PCT/IB2017/052382 dated Aug. 17, 2017.
(Continued)

*Primary Examiner* — Katherine M Shi
(74) *Attorney, Agent, or Firm* — Middleton Reutlinger

(57) ABSTRACT

Some implementations provide a high-powered compact ultrasonic transducer having an integral piezoelectric ceramic force sensing element utilized to enable enhanced tissue selectivity with a piezoelectric based transducer. Some implementations additionally or alternatively relate to methods and apparatus for driving ultrasonic surgical devices, such as methods and apparatus that modulate an amplitude of a drive signal, provided to an ultrasonic surgical device, in accordance with a selected tissue selectivity level. For example, the amplitude of the drive signal for a given tissue selectivity level can be varied with time in accordance with amplitude modification parameters that are particularized to the given tissue selectivity level. Some of those implementations additionally implement a corresponding duty cycle, for the drive signal, that corresponds to the selected tissue selectivity level.

16 Claims, 21 Drawing Sheets

(51) Int. Cl.
*B06B 1/06* (2006.01)
*A61B 17/00* (2006.01)
(52) U.S. Cl.
CPC .............. *A61B 2017/00146* (2013.01); *A61B 2017/00185* (2013.01); *A61B 2017/00973* (2013.01); *A61B 2017/32007* (2017.08); *A61B 2017/320069* (2017.08); *A61B 2217/005* (2013.01); *B06B 2201/76* (2013.01)
(58) Field of Classification Search
CPC ....... A61B 2017/320069; A61B 2017/320089; A61B 2017/320093; A61B 2017/320071; A61B 2017/320088; A61B 2017/00017; A61B 2217/005; A61B 2017/00106; A61B 2018/00994; A61B 2217/007; A61B 2018/00577; A61B 2018/00642; A61N 7/02; A61N 7/00; A61N 7/022; A61F 9/00745; B06B 2201/76
See application file for complete search history.

(56) References Cited

U.S. PATENT DOCUMENTS

| | | | |
|---|---|---|---|
| 4,425,115 A | 1/1984 | Wuchinich | |
| 4,516,398 A | 5/1985 | Wuchinich | |
| 4,634,419 A | 1/1987 | Kreizman et al. | |
| 4,734,964 A | 4/1988 | Lane et al. | |
| 4,747,820 A | 5/1988 | Hornlein et al. | |
| 4,750,902 A | 6/1988 | Wuchinich et al. | |
| 4,768,496 A | 9/1988 | Kreizman et al. | |
| 4,827,911 A | 5/1989 | Broadwin et al. | |
| 4,846,790 A | 7/1989 | Hornlein et al. | |
| 4,881,761 A | 11/1989 | Hornlein et al. | |
| 4,921,476 A | 5/1990 | Wuchinich | |
| 4,931,047 A | 6/1990 | Broadwin et al. | |
| 4,978,333 A | 12/1990 | Broadwin et al. | |
| 4,988,334 A | 1/1991 | Hornlein et al. | |
| 5,015,227 A | 5/1991 | Broadwin et al. | |
| 5,190,517 A | 3/1993 | Zieve et al. | |
| 5,221,282 A | 6/1993 | Wuchinich | |
| 5,421,829 A | 6/1995 | Olichney et al. | |
| 5,466,020 A | 11/1995 | Page et al. | |
| 5,484,398 A | 1/1996 | Stoddard | |
| D367,323 S | 2/1996 | Carr | |
| 5,492,528 A | 2/1996 | Anis | |
| 5,984,904 A | 11/1999 | Steen et al. | |
| 6,083,191 A | 7/2000 | Rose | |
| 6,177,755 B1 | 1/2001 | Hur | |
| D438,952 S | 3/2001 | Cimino et al. | |
| 6,214,017 B1 | 4/2001 | Stoddard et al. | |
| 6,256,859 B1 | 7/2001 | Stoddard et al. | |
| 6,319,223 B1 | 11/2001 | Wortrich | |
| 6,468,059 B2 | 10/2002 | Haser | |
| 6,499,358 B1 | 12/2002 | Hogan et al. | |
| D477,867 S | 7/2003 | O'Mahony | |
| 6,595,957 B1 | 7/2003 | Griffiths | |
| 6,602,227 B1 | 8/2003 | Cimino et al. | |
| D479,320 S | 9/2003 | O'Mahony | |
| 6,654,999 B2 | 12/2003 | Stoddard et al. | |
| 6,723,110 B2 | 4/2004 | Timm et al. | |
| 7,204,825 B2 | 4/2007 | Cimino et al. | |
| D557,804 S | 12/2007 | Muri | |
| 7,442,168 B2 | 10/2008 | Novak et al. | |
| 7,871,392 B2 | 1/2011 | Sartor | |
| 8,092,475 B2 | 1/2012 | Cotter et al. | |
| 8,118,823 B2 | 2/2012 | Cotter et al. | |
| 8,142,460 B2 | 3/2012 | Cotter et al. | |
| 8,211,103 B2 | 7/2012 | Greep | |
| D675,728 S | 2/2013 | Tout | |
| 8,518,066 B2 | 8/2013 | Cotter et al. | |
| D699,836 S | 2/2014 | Burger | |
| 9,149,291 B2 | 10/2015 | Parham et al. | |
| 9,421,027 B2 | 8/2016 | Cotter et al. | |
| D557,803 S | 12/2017 | Muri | |
| 2002/0002369 A1 | 1/2002 | Hood | |
| 2006/0052774 A1 | 3/2006 | Garrison et al. | |
| 2006/0063973 A1 | 3/2006 | Makower et al. | |
| 2008/0200884 A1 | 8/2008 | Perkins et al. | |
| 2011/0160620 A1 | 6/2011 | Gill et al. | |
| 2012/0209303 A1* | 8/2012 | Frankhouser | A61B 10/025 606/169 |
| 2014/0005667 A1* | 1/2014 | Stulen | A61B 34/37 606/45 |
| 2015/0080925 A1 | 3/2015 | Schulte et al. | |
| 2015/0328048 A1 | 11/2015 | Koplin | |
| 2017/0304655 A1 | 10/2017 | Cotter et al. | |
| 2017/0333606 A1 | 11/2017 | Manandhar et al. | |
| 2017/0354429 A1 | 12/2017 | Ketelhohn et al. | |

FOREIGN PATENT DOCUMENTS

| | | |
|---|---|---|
| JP | H0199547 A | 4/1989 |
| WO | 9308750 A2 | 5/1993 |
| WO | 9517855 | 7/1995 |
| WO | 2004045705 | 6/2004 |
| WO | 2008154803 A1 | 12/2008 |
| WO | 2010057211 A1 | 5/2010 |
| WO | 2011005467 A2 | 1/2011 |
| WO | 2014134292 | 9/2014 |
| WO | 2015061258 | 4/2015 |
| WO | 2017187345 | 11/2017 |
| WO | 2017203408 | 11/2017 |

OTHER PUBLICATIONS

International Search Report and Written Opinion for PCT/IB2017/052980 dated Jul. 19, 2017.
International Search Report and Written Opinion for PCT/IB2017/053510 dated Nov. 13, 2017.
Partial Search Report for PCT/IB2017/053510 dated Sep. 22, 2017.
Franasiak, Jason M.; Ergonomic Strain in Minimally Invasive Surgery: Addressing the Strain Epidemic; www.jcomjournal.com; vol. 22, No. 6, pp. 267-273, Jun. 2015.
Krautkramer J. and Krautkramer H., Ultrasonic Testing of Materials, 1983.
Berguer, R.; Ergonomic problems associated with laparoscopic surgery; Surgical Endoscopy, 1999 13: 466-468; 1999.
Integra Lifesciences Corporation; CUSA Excel Ultrasonic Surgical Aspiration System, CUSA EXcel System User's Guide, 6 pages, 2007.
Integra Lifesciences Corporation; CUSA Excel+ Ultrasonic Surgical Aspirator, 8 pages, 2012.
SonaStar; Ultrasonic surgical aspiration system; Accuracy Matters, 2015.
Partial Search for International Application No. PCT/IB2017/057145 dated Jan. 31, 2018.
Transmittal Letter of Related Cases dated Jan. 30, 2019.
European Patent Office, International Search Report and Written Opinion for PCT/IB2017/057145 dated Mar. 15, 2018, mailed Mar. 23, 2018, Rijswijk, NL.

\* cited by examiner

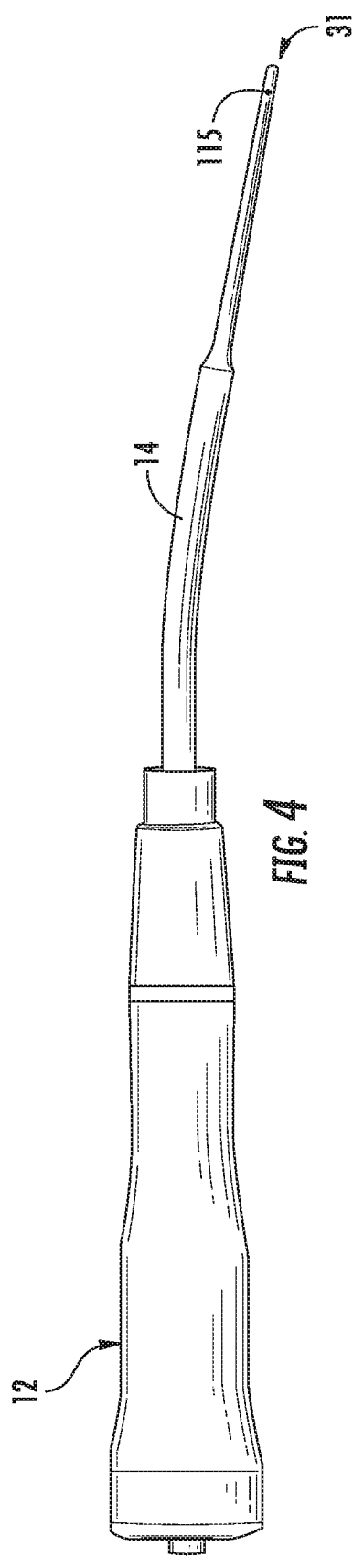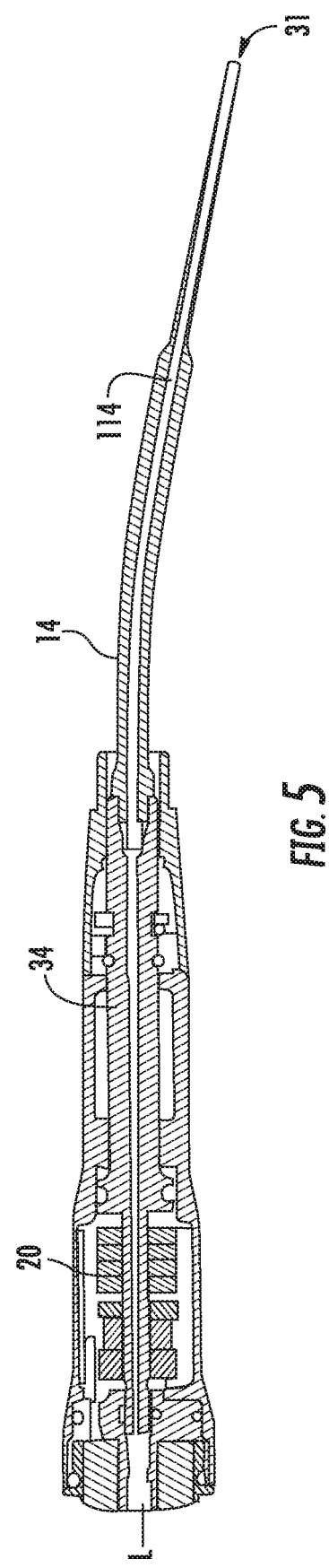

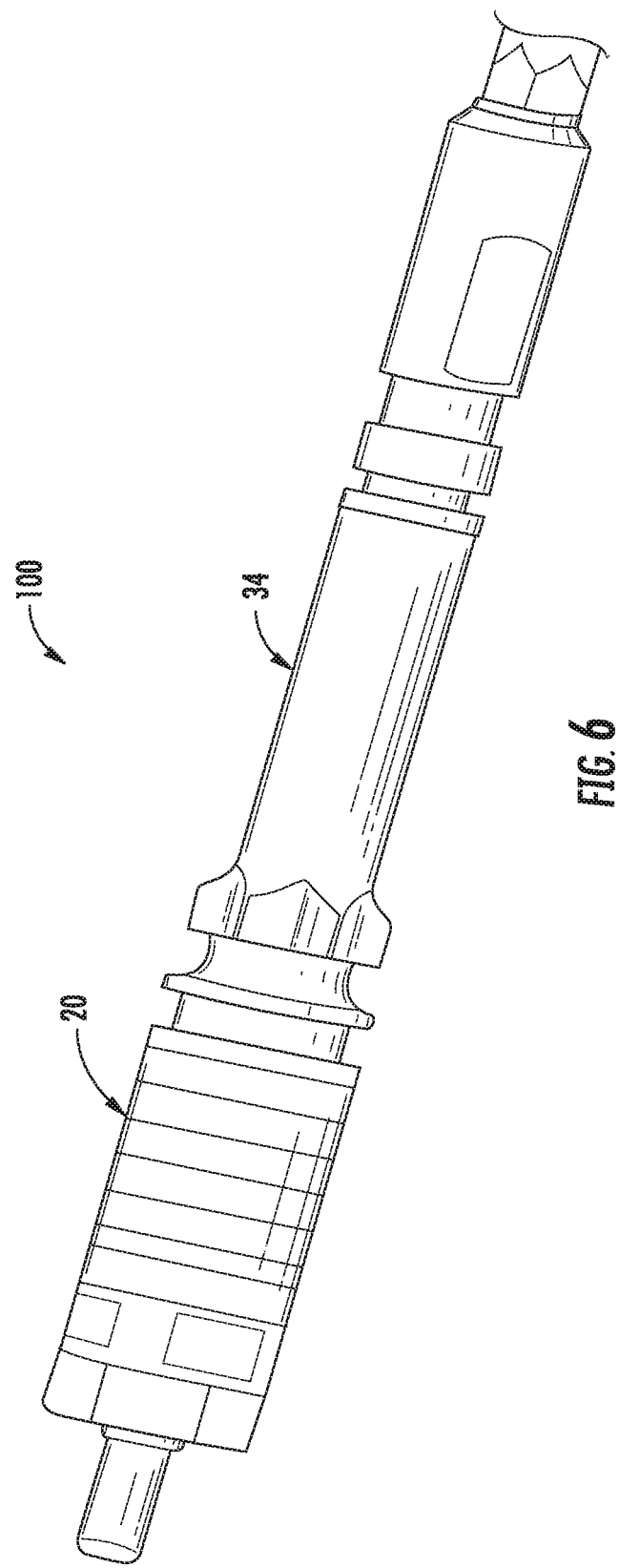

AFTER KRAUTKRAMER, ENSMINGER, et al, WHERE
W=Work   F=Force   D=Distance   $P_{wr}$=Power
t= time   V= Velocity   P=Pressure   S=Cross-Section Area
$I_0$=Intensity   $\rho$=density   $\varepsilon$=displacement   $\omega$= $2\pi f$ =angular frequency
f=frequency $Z_c$= Characteristic Acoustic Impedance   Z=Acoustic Impedance

CAVITATION THRESHOLDS

| TIP SELECTION | LIQUID | STROKE (μm) | ACOUSTIC POWER (W) | CONTACT AREA (mm$^2$) | INTENSITY (kW/m$^2$) | PRESSURE (kPa) |
|---|---|---|---|---|---|---|
| 36 kHz EXTENDED MICROTIP | WATER | 167 | 3.44 | 19.4 | 177 | 94 |
| | SALINE | 152 | 3.70 | 19.4 | 190 | 111 |
| 23 kHz STANDARD TIP | WATER | 266 | 5.90 | 25.8 | 229 | 119 |
| | SALINE | 216 | 5.50 | 25.8 | 213 | 136 |

| | TISSUE SELECT | Vp-MAX | STROKE (μm) | CAVITATION SALINE |
|---|---|---|---|---|
| 23 kHz STANDARD TIP | Std | 3.20 | 356 | YES |
| | + | 3.12 | 347 | YES |
| | ++ | 3.04 | 338 | YES |
| | +++ | 2.80 | 311 | INTERMITTENT |
| | ++++ | 2.16 | 240 | NO |

FIG. 9

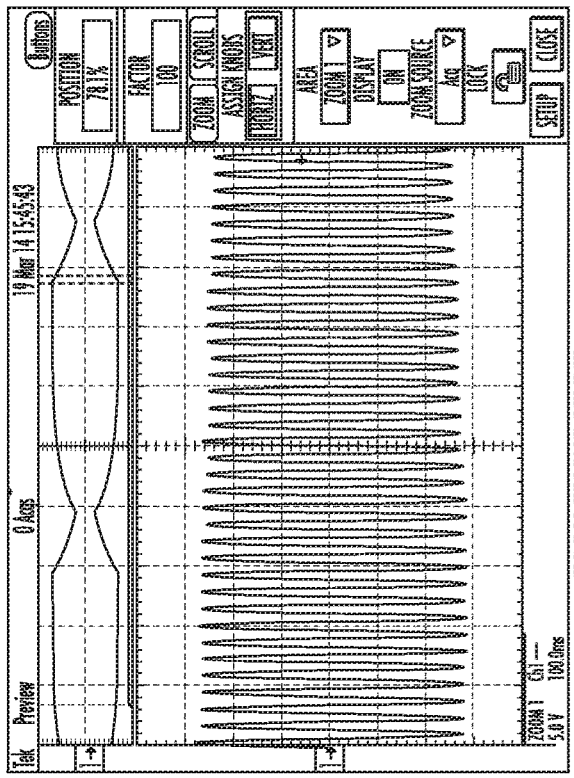
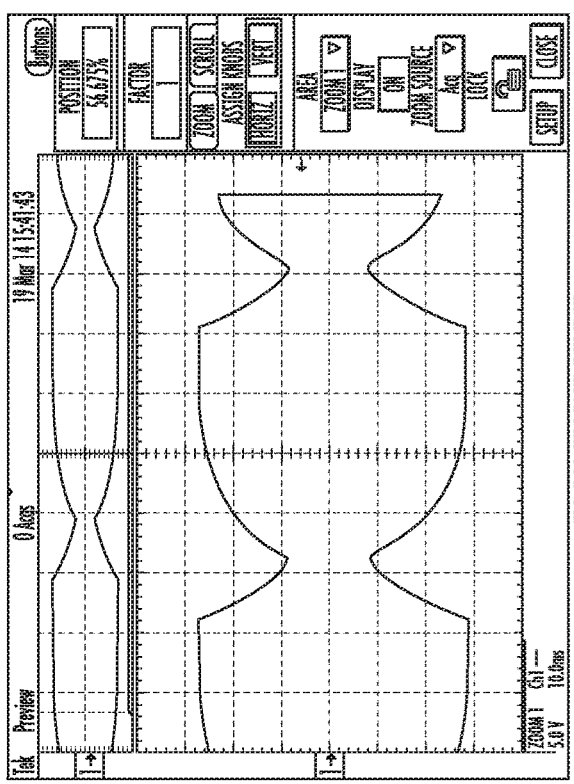
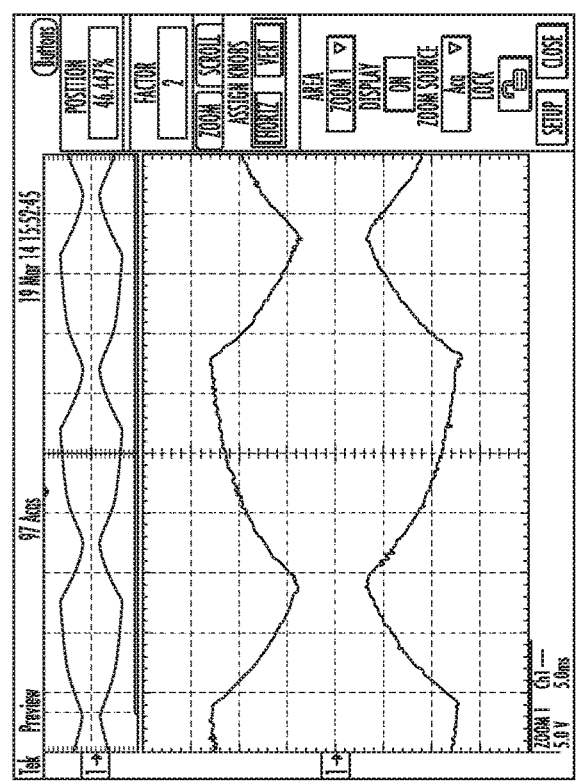
FIG. 11

ULTRASONIC TRANSDUCER TISSUE SELECTIVITY

CROSS-REFERENCE TO RELATED APPLICATIONS

This application claims priority to and benefit under 35 U.S.C. § 119 to U.S. Provisional Application No. 62/423,407, filed Nov. 17, 2016, the entire contents of which are hereby incorporated by reference.

TECHNICAL FIELD

Some implementations disclosed herein relate generally to ultrasonic surgical devices, and more particularly, to ultrasonic surgical aspirators or tissue ablation systems for removing diseased tissues. Some implementations disclosed herein additionally or alternatively relate to methods and apparatus for driving ultrasonic surgical devices, such as methods and apparatus that modulate an amplitude of a drive signal, provided to an ultrasonic surgical device, in accordance with a selected tissue selectivity level. For example, the amplitude of the drive signal for a given tissue selectivity level can be varied with time in accordance with amplitude modification parameters that are particularized to the given tissue selectivity level. Some of those implementations additionally implement a corresponding duty cycle, for the drive signal, that corresponds to the selected tissue selectivity level.

BACKGROUND

Ultrasonic aspiration has become the standard of care for removal of tumors and diseased tissue in neurosurgery and general surgery. Typically, ultrasonic surgical aspirators for fragmenting and aspirating tissue include an ultrasonic transducer supported within a handpiece, an ultrasonically vibrating horn or tip operably connected to the ultrasonic transducer, and a flue positioned about the horn. The horn includes a longitudinally extending central bore having one end located adjacent a distal tip and a second end located adjacent the proximal end of the horn. The proximal end of the horn is adapted to engage a vacuum source to facilitate aspiration of fluid. The flue is positioned about the horn to define an annular passage. Irrigation fluid such as saline is supplied through the annular passage around the horn to the surgical site where it mixes with blood and tissue particles and is aspirated through the bore in the horn. By mixing the irrigation fluid with the blood and tissue particles, coagulation of the blood is slowed down and aspiration thereof is aided. U.S. Pat. Nos. 5,015,227 and 4,988,334 disclose such ultrasonic surgical devices and are incorporated herein by reference. For example, a titanium surgical tip may be powered by a transducer to fragment tissue and suction effluent via a central channel. The transducer vibrates along its length, and ultrasonic horns such as stepped horns and specialty profiles of reduced diameter amplify vibration.

The Ampulla or Gaussian profile was published by Kleesattel as early as 1962, and is employed as a basis for many ultrasonic horns in surgical applications including devices for use in ultrasonic aspiration as described in U.S. Pat. No. 4,063,557 to Wuchinich, et al, 1977, and U.S. Pat. No. 6,214,017 to Stoddard, et al, 2001, which are incorporated herein by reference. The Gaussian profile is used in practice to establish and control the resonance and mechanical gain of horns. A resonator, a connecting body, and the horn act together as a three-body system to provide a mechanical gain, which is defined as the ratio of output stroke amplitude of the distal end of the tip to the input amplitude of the resonator. The mechanical gain is the result of the strain induced in the materials of which the resonator, the connecting body, and the ultrasonic horn are composed.

A magnetostrictive transducer coupled with the connecting body functions as a first stage of the booster horn with a mechanical gain of about 2:1, due to the reduction in area ratio of the wall of the complex geometry. The major diameter of the horn transitions to the large diameter of the Gaussian segment in a stepped-horn geometry with a gain of as large as about 5:1, again due to reduction in area ratio. The uniform strain along the length of the Gaussian provides multiplicative gain of typically less than 2:1. Thus, the application of ultrasonically vibrating surgical devices used to fragment and remove unwanted tissue with significant precision and safety has led to the development of a number of valuable surgical procedures.

Certain devices known in the art characteristically produce continuous vibrations having substantially constant amplitude at a frequency of about twenty to about fifty-five kHz, for example, at a predetermined frequency of 20-36 kHz. Amplitude of vibration of transducer-surgical tip systems decreases with increasing frequency because maximum stress in the material of the horns is proportional to amplitude times frequency, and the material must be maintained to an allowed fraction of its yield strength to support rated life in view of material fatigue limits. For example, U.S. Pat. Nos. 4,063,557, 4,223,676 and 4,425,115, which are incorporated herein by reference, disclose devices suitable for the removal of soft tissue which are particularly adapted for removing highly compliant elastic tissue mixed with blood. Such devices are adapted to be continuously operated when the surgeon wishes to fragment and remove tissue, and generally is operated by a foot switch.

In an apparatus that fragments tissue by the ultrasonic vibration of a surgical tip, efficiency of energy utilization is optimized when the transducer which provides the ultrasonic vibration operates at resonant frequency. The transducer and surgical tip design establishes the resonant frequency of the system, while the generator tracks the resonant frequency and produces the electrical driving signal to vibrate the transducer at the resonant frequency. However, changes in operational parameters, such as changes in temperature, thermal expansion, and load impedance, result in deviations in the resonant frequency. Accordingly, controlled changes in the frequency of the driving signal are required to track the resonant frequency. This is controlled automatically in the generator.

Conventional ultrasonic surgical aspirating tips employed in surgery for many years typically present a longitudinally vibrating annular surface with a central channel providing suction or aspiration, which contacts tissue and enables fragmentation via described mechanisms of mechanical impact (momentum), cavitation, and ultrasound propagation. Mechanical impact may be most useful in soft tissue and cavitation clearly contributes to the fragmentation of tenacious and hard tissue in situations where liquids are present and high intensity ultrasound exceeds the cavitation threshold.

Ultrasound propagation is concerned with the transmission of pressure across the boundary of a surgical tip and tissue, which leads to the propagation of pressure and, perhaps more importantly, particle displacement. Acoustic impedance is the total reaction of a medium to acoustic transmission through it, represented by the complex ratio of the pressure to the effective flux, that is, particle velocity times surface area through the medium. As discussed in the classic text of Krautkramer J. and Krautkramer H, Ultrasonic Testing of Materials, Berlin, Heidelberg, N.Y., 1983, for the case of a low to high acoustic impedance boundary, it may seem paradoxical that pressure transmitted can exceed 100%, but that is what results from the build-up of pressure from a low to high acoustic impedance boundary. In the case of a high to low acoustic impedance mismatch, such as with a high impedance titanium ultrasonic horn to low impedance fibrous muscle, soft tissue, or water, the pressure transmitted decreases (e.g., less than 15% for titanium to fibrous muscle) and particle displacement increases (e.g., as great as 186% for titanium to muscle).

U.S. Pat. No. 4,827,911 to Broadwin et al., 1989, described the use of a periodically interrupted power supply to limit thermal rise of tissue at the surgical site. This is referred to as pulse width modulation hereinafter. The patent described the use of periodic interruption of power, or pulse width modulation, to control reserve power independently of stroke, such that fragmentation power, now known to be associated with velocity squared or stroke times frequency all squared, could be maintained for efficacy in tissue removal. A system was implemented to modulate between only a high amplitude and low amplitude. It improved potential for safe use of the ultrasonic aspirators with implementation of periodic interruption of power supplied with an electronically derived analog duty cycle. The duty cycle could simply be on and off, but was implemented as a duty cycle from a high amplitude to lower amplitude versus an on and off state. It is noted that the steady state stroke is also shown as decreasing with increased tissue selectivity settings. It appeared that the primary interest was to limit reserve power or transducer power to the surgical site, which could cause heating. Temperature feedback was discussed in the patent.

U.S. Pat. No. 6,083,191 to Rose et al., 2000, described the introduction of a sense ceramic in the piezoelectric stack, and described its use as a means of controlling stroke. In the later implementation, a limiter was used to control power electronically, and it was said this provided tissue selectivity enhancement.

A known instrument on the market for the ultrasonic fragmentation of tissue at an operation site and aspiration of the tissue particles and fluid away from the site is the CUSA® Excel Ultrasonic Surgical Aspirator (Integra LifeSciences Corporation, Plainsboro, N.J.). When the longitudinally vibrating tip in such an aspirator is brought into contact with tissue, it fragments and removes the tissue. In simple harmonic motion devices, the frequency is independent of amplitude. CUSA Excel magnetostrictive transducers utilized a magnetic feedback coil and circuit to monitor stroke.

The devices described above suffered from one or more drawbacks. For example, such devices did not provide proper tissue selectivity over the full amplitude range of operation. For instance, they did not necessarily enable precise tissue selectivity at low amplitudes (e.g., below 50% amplitude settings). Also, for instance, control of reserve power in such devices does not function correctly at low amplitudes, and these low amplitudes are often employed in neurosurgery. In neurosurgery practice, such as removal of glioma tumors, it is found 30% or lower amplitude is often employed and the control of the reserve power with analog control of such devices is not functional. In fact, higher reserve power could occur with some settings of higher selectivity.

Hence, for these and other reasons, there is a need for a surgical handpiece with improved tissue selection function. The present disclosure fulfills this need and others.

SUMMARY

Some implementations disclosed herein provide a high-powered compact ultrasonic transducer having an integral piezoelectric ceramic force sensing element (also referred to herein as a "sense ceramic") utilized in a novel way to enable enhanced tissue selectivity with a piezoelectric based transducer. The integral piezoelectric ceramic force sensing element is utilized in a way separating surgical tip stroke and power control, which was previously implemented with pickup coils on magnetostrictive transducers. The separation of surgical tip stroke and power control helps limit power and thermal rise to the surgical site, and helps control propensity for cavitation in preserving viscoelastic collagen rich tissue. The sense ceramic enables implementation of a tissue selection feature that is helpful to general and neurosurgery practices.

Some implementations disclosed herein additionally or alternatively relate to methods and apparatus for driving ultrasonic surgical devices, such as methods and apparatus that modulate an amplitude of a drive signal, provided to an ultrasonic surgical device, in accordance with a selected tissue selectivity level. For example, the amplitude of the drive signal for a given tissue selectivity level can be varied with time in accordance with amplitude modification parameters that are particularized to the given tissue selectivity level. Some of those implementations additionally implement a corresponding duty cycle, for the drive signal, that corresponds to the selected tissue selectivity level.

In some implementations, an ultrasonic surgical apparatus is provided for performing a surgical procedure at a surgical site on a patient at different tissue selectivity levels. The ultrasonic surgical apparatus includes a handpiece; a surgical tool coupled to the transducer and having a surgical tip for transmitting ultrasonic waves from the transducer to the surgical site; a transducer disposed in the handpiece and having a sense ceramic that provides a voltage proportional to stress or charge proportional to deflection of the surgical tip; and microcontroller firmware that is hardcoded with a look-up table for creating predetermined wave shapes of outputs that correspond to predetermined tissue selectivity levels.

In some of those implementations, the transducer in the ultrasonic surgical apparatus includes an integral piezoelectric ceramic force sensing element that separates surgical tip stroke and power control. In addition, the look-up table is used for creating predetermined wave shape outputs that provide simultaneous pulse width modulation and amplitude modulation.

In some implementations, an ultrasonic surgical apparatus is provided for performing a surgical procedure at a surgical site. The ultrasonic surgical apparatus includes a handpiece, at least one drive ceramic disposed in the handpiece, and a surgical tip mechanically coupled to the drive ceramic. The drive ceramic is electrically coupled to at least one controller that selectively generates dynamic output for driving the drive ceramic, and the drive ceramic generates corresponding ultrasonic waves in response to being driven by the dynamic output. The surgical tip transmits the ultrasonic waves, generated by the drive ceramic, to the surgical site. The ultrasonic surgical apparatus also includes at least one sense ceramic disposed in the handpiece. The sense ceramic provides a sense electrical output that corresponds to deflection of the surgical tip.

Those and other implementations can include one or more of the following features.

In some implementations, at each control cycle of a plurality of control cycles, the controller generates the dynamic output at the control cycle based on the sense electrical output at the control cycle and based on controlling an amplitude of the dynamic output in accordance with a corresponding amplitude modification parameter for the control cycle. In some of those implementations, the corresponding amplitude modification parameter is utilized in controlling the amplitude at the control cycle based on being one of multiple amplitude modification parameters stored in association with a currently selected tissue selectivity level. In some versions of those implementations, when the currently selected tissue selectivity level is selected, the controller generates the dynamic output to provide simultaneous pulse width modulation and amplitude modulation, in the dynamic output, that is particularized to the selected tissue selectivity level. In some additional or alternative versions of those implementations: at a first control cycle of the plurality of control cycles, the controller generates the dynamic output at the first control cycle based on controlling the amplitude in accordance with a first amplitude modification parameter of the multiple modification parameters; at a second control cycle of the plurality of control cycles, the controller generates the dynamic output at the second control cycle based on controlling the amplitude in accordance with a second amplitude modification parameter of the multiple modification parameters; and at a third control cycle of the plurality of control cycles, the controller generates the dynamic output at the third control cycle based on controlling the amplitude in accordance with a third amplitude modification parameter of the multiple modification parameter.

In some implementations a method of modulating amplitude of a drive signal applied to at least one transducer of an ultrasonic surgical apparatus is provided. The method includes: identifying a selection of a particular tissue selectivity level, the particular tissue selectivity level being one of a plurality of available tissue selectivity levels; and determining particular waveform modification parameters for the particular tissue selectivity level. The particular waveform modification parameters are particularized to the particular tissue selectivity level and are determined based on being stored, in one or more computer readable media, in association with the particular tissue selectivity level. The method further includes, in response to the selection of the particular tissue selectivity level and until occurrence of a stop condition: generating the drive signal based on the particular waveform modification parameters.

Those and other implementations can include one or more of the following features.

In some implementations, generating the drive signal based on the particular waveform modification parameters includes: selectively modifying a feedback based reference drive signal based on the particular waveform modification parameters to generate the drive signal with an amplitude that is modulated based on the particular waveform modification parameters that are stored in association with the particular tissue selectivity level. In some versions of those implementations, the particular waveform modification parameters include three or more discrete values each indicating an extent by which to reduce a reference amplitude of the feedback based reference signal in modifying the feedback based reference drive signal to generate the drive signal with the amplitude that is modulated. In some of those versions, selectively modifying the feedback based reference drive signal based on the particular waveform modification parameters includes: at a first control cycle, reducing the reference amplitude of the feedback based reference drive signal by a first extent that is based on a first discrete value of the three or more discrete values, at a second control cycle, reducing the reference amplitude of the feedback based reference drive signal by a second extent that is based on a second discrete value of the three or more discrete values, and at a third control cycle, reducing the reference amplitude of the feedback based reference drive signal by a third extent that is based on the third discrete value of the three of more discrete values. The second control cycle can optionally immediately follow the first control cycle—or one or more intermediate control cycles can be interposed between the first control cycle and the second control cycle. When one or more intermediate control cycles are interposed, modifying the feedback based reference drive signal based on the particular waveform modification parameters can optionally further include: at each of the intermediary control cycles, reducing the reference amplitude of the feedback based reference drive signal by the first extent that is based on the first discrete value of the three or more discrete values. In some implementations, selectively modifying the feedback based reference drive signal based on the particular waveform modification parameters further includes: at a fourth control cycle, maintaining the reference amplitude of the feedback based reference drive signal based on a fourth discrete value of the three or more discrete values. In some implementations, the three or more discrete values are stored with an indication of a sequence of the three or more discrete values, and selectively modifying the feedback based reference drive signal based on the particular waveform modification parameters to generate the drive signal with the amplitude that is modulated based on the particular waveform modification parameters includes: at one or more first control cycles, reducing the reference amplitude of the feedback based reference drive signal by a first extent that is based on a first discrete value of the three or more discrete values; at one or more second control cycles that immediately follow the one or more first control cycles, reducing the reference amplitude of the feedback based reference drive signal by a second extent that is based on a second discrete value of the three or more discrete values. The second discrete value is utilized at the one or more second control cycles based on the second discrete value following the first discrete value in the sequence, and based on the one or more second control cycles immediately following the one or more first control cycles.

In some implementations, the waveform modification parameters define a particular duty cycle that is particularized to the particular tissue selectivity level, and the waveform modification parameters further define three or more values that are each utilized to determine the amplitude at a corresponding segment of the duty cycle.

In some implementations, the waveform modification parameters include twenty or more sequential discrete values, and selectively modifying the feedback based reference drive signal based on the particular waveform modification parameters includes cycling through the sequential discrete values in sequence to selectively modify, at each of a plurality of control cycles, the feedback based reference drive signal based on a corresponding one of the sequential discrete values.

In some implementations, the waveform modification parameters are stored in a look-up table in the one or more computer readable media. For example, the one or more computer readable media can include non-volatile memory.

In some implementations, identifying the selection of the particular tissue selectivity level is based on user interface input received in response to interaction of a surgeon with one or more user interface input devices. In some of those implementations, the one or more user interface input devices include a foot pedal.

In some implementations, the stop condition includes identifying a selection of an additional tissue selectivity level of the plurality of available tissue selectivity levels. In some of those implementations, the method further includes: identifying the selection of the additional tissue selectivity level; determining additional waveform modification parameters for the additional tissue selectivity level, wherein the additional waveform modification parameters differ from the particular waveform modification parameters, and wherein the additional waveform modification parameters are determined based on being stored, in one or more of the computer readable media, in association with the additional tissue selectivity level; in response to the selection of the additional tissue selectivity level and until occurrence of another stop condition: generating the drive signal based on the additional waveform modification parameters, wherein generating the drive signal based on the additional waveform modification parameters includes: selectively modifying the feedback based reference drive signal based on the additional waveform modification parameters to generate the drive signal with the amplitude being modulated based on the additional waveform modification parameters that are stored in association with the additional tissue selectivity level.

In some implementations, the stop condition includes a stop command that is based on user interface input received in response to interaction of a surgeon with one or more user interface input devices.

In some implementations, the method further includes generating the feedback based reference drive signal based on sense electrical output received from a sense ceramic mechanically coupled with the at least one transducer.

In some implementations, a method of modulating pulse width and amplitude of a drive signal applied to at least one transducer of an ultrasonic surgical apparatus is provided, and includes: in response to selection of a first tissue selectivity level of a plurality of available tissue selectivity levels: generating the drive signal using first pulse width modulation parameters and first amplitude modulation parameters that are particularized to the first tissue selectivity level; and in response to selection of a second tissue selectivity level of the plurality of available tissue selectivity levels: generating the drive signal using second pulse width modulation parameters and second amplitude modulation parameters that are particularized to the second tissue selectivity level, wherein the second pulse width modulation parameters differ from the first pulse width modulation parameters and the second amplitude modulation parameters differ from the first amplitude modulation parameters.

Those and other implementations can include one or more of the following features.

In some implementations, the first amplitude modulation parameters cause adjustment of the amplitude of the drive signal to three or more extents during a duty cycle that is dictated by the first pulse width modulation parameters.

Various implementations disclosed herein may include one or more controllers utilized in performance of all or aspects of one or more of the methods described herein. The term "controller" is used herein generally to describe various apparatus relating to the adaptation of amplitude and/or duty cycle, of a drive signal provided to an ultrasonic surgical device, in accordance with a selected tissue selectivity level. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various implementations include, but are not limited to, conventional microprocessors, application specific integrated circuits (ASICs), and field-programmable gate arrays (FPGAs).

In various implementations, a processor or controller may be associated with one or more storage media (generically referred to herein as "memory" e.g., volatile and non-volatile computer memory such as RAM, PROM, EPROM, and EEPROM, etc.). In some implementations, the memory may be encoded with one or more programs that, when executed by corresponding controller(s), perform at least some of the functions discussed herein. Memory may be fixed within a processor or controller or may be transportable, such that the one or more programs stored thereon can be loaded into a processor or controller so as to implement various aspects of implementations disclosed herein.

Other features and advantages of the present disclosure will become more apparent from the following detailed description, when taken in conjunction with the accompanying drawings.

BRIEF DESCRIPTION OF THE DRAWINGS

Implementations are described herein with reference to the drawings, in which:

FIG. 4 is a side view of an ultrasonic surgical handpiece in accordance with various implementations, and with a nosecone and surgical tip attached to it;

FIG. 5 is a longitudinal-sectional view of the device shown in FIG. 4;

FIG. 6 is a perspective view of a piezoelectric transducer stack assembly in accordance with various implementations;

FIG. 9 is a summary of thresholds of cavitation in liquid including the calculated pressure at given velocity the surgical tips of different frequencies, along with sample observations of a 23 kHz Standard Tip;

FIG. 11 shows characteristic waveforms;

FIG. 20 shows finer control of reserve power at low amplitudes in accordance with various implementations, with curved EMT tip, 100% amplitude setting, 406 V (r.m.s) max drive, 15 events per TS-setting with 15 s breaks. CUSA Excel handpiece: 35.86 kHz, 22.4 W, stroke=0.0073 in.

DETAILED DESCRIPTION

Figure 1:
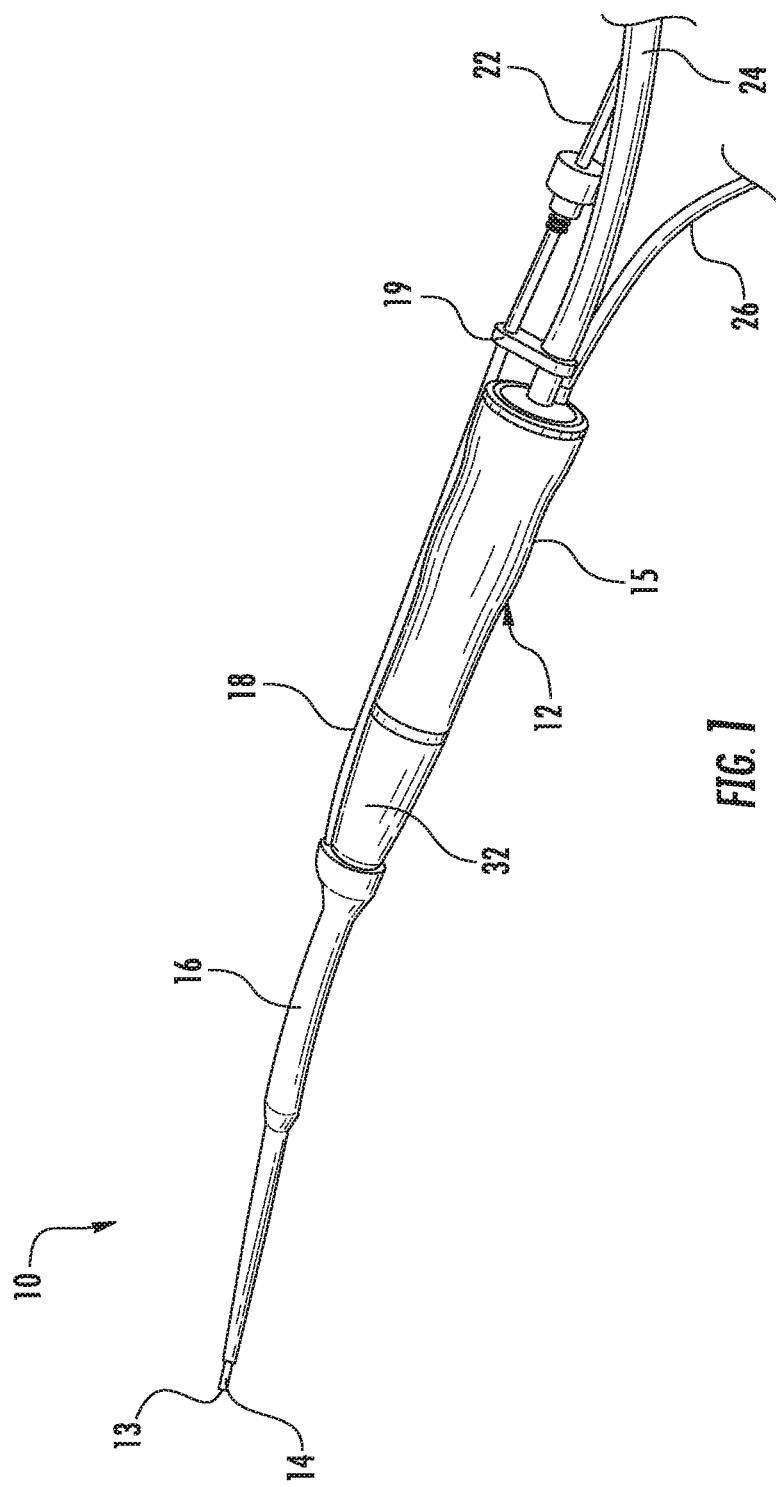
FIG. 1 is a perspective view of an ultrasonic surgical apparatus in accordance with various implementations.
Figure 2:
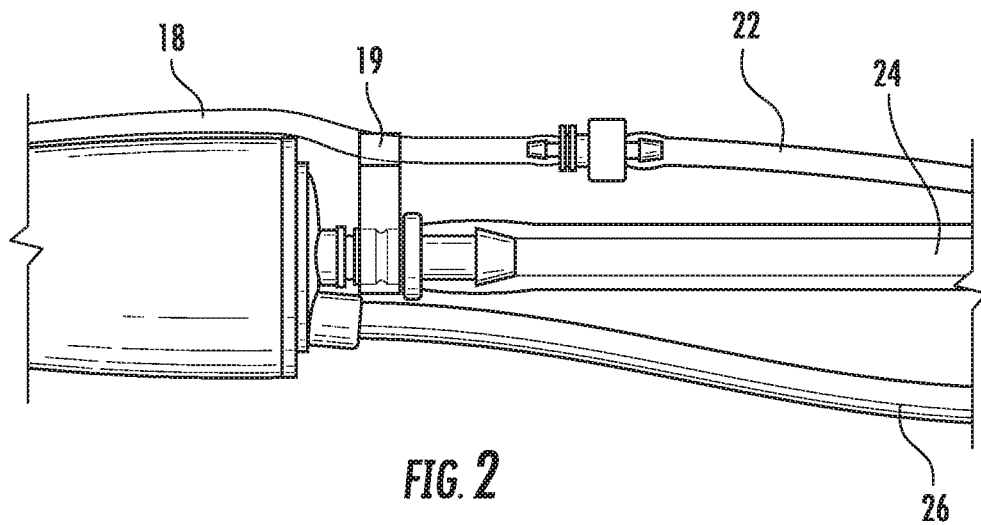
FIG. 2 illustrates the proximal end of the apparatus of FIG. 1 in more detail.
Figure 3:
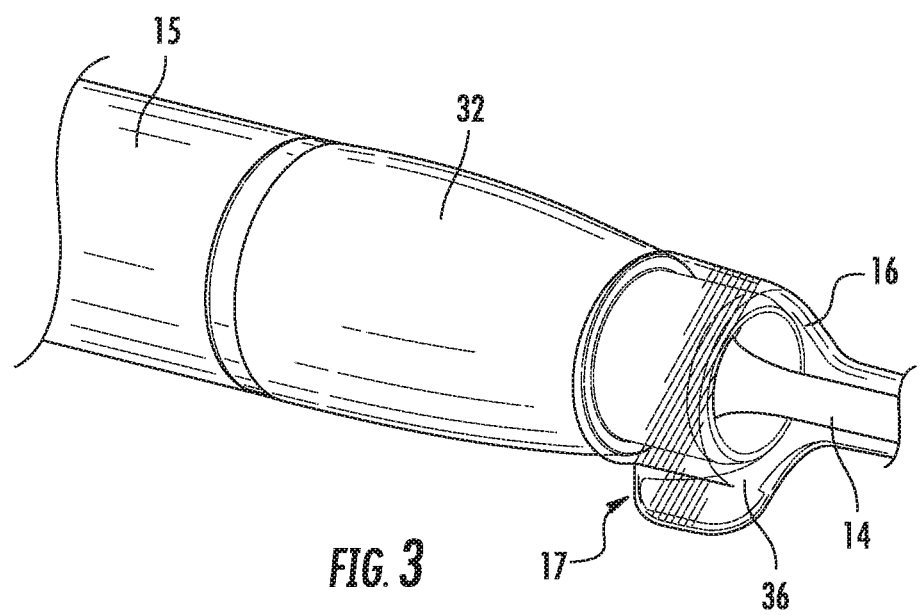
FIG. 3 is a perspective view a nosecone fully assembled to a handpiece and supporting a flue (the flue tube is not shown in this drawing)

Implementations will now be described in detail with reference to the drawings, in which like reference numerals designate identical or corresponding elements in each of the several views. As used herein, the term "distal" refers to that portion of the instrument, or component thereof which is farther from the user while the term "proximal" refers to that portion of the instrument or component thereof which is closer to the user during normal use. The terms "ultrasonic horn," "ultrasonic tip," "ultrasonic aspirating tip," "ultrasonic surgical aspirating tip," "aspirating tip," "ultrasonic surgical tip," "surgical tip" and "tip" are used herein interchangeably.

Referring now to FIGS. 1-5, one implementation of an ultrasonic surgical apparatus is shown. The ultrasonic surgical apparatus 10 can be used for ultrasonically fragmenting and aspirating tissue in a surgical operation. The ultrasonic surgical apparatus 10 includes a handpiece 12 used by a surgeon to direct fragmentation. The handpiece 12 encases a transducer on which a surgical tip or ultrasonic horn 14 is fastened. The ultrasonic horn 14 can be powered by the transducer through an internal horn 34 and be ultrasonically actuated to fragment tissue and suction effluent via a central channel or throughbore 114. A distal end portion 13 of the ultrasonic horn 14 extends beyond a distal end of the flue 16. The ultrasonic horn 14 is vibrated to fragment tissue during surgery. The ultrasonic horn may be made of titanium or other material(s), such as other conventional material(s) known in the art.

A cooling and irrigation system which provides cooling fluid to the ultrasonic horn 14 is provided for maintaining temperature within an acceptable range. The handpiece 12 includes a housing 15 which may be formed of a sterilizable plastic or metal. The flue 16 provides a path for irrigation fluid or liquid and connects to the distal end of the housing 15. The flue 16 typically interfaces to the handpiece 12 via a nosecone 32. The flue 16 may include or attach to a flue tube 18 and be in fluid communication with the flue tube 18 through an opening 17. The nosecone 32 attaches to the handpiece 12 and covers the internal portion of the ultrasonic horn 14.

An irrigation tube 22 connects to the flue tube 18 upstream and supplies irrigation fluid through the flue tube 18 to an operative site during surgery. An aspiration tube 24 provides suction and a path for aspiration from the operative site to a collection canister (not shown). A flue tube clip 19 allows for adjustment of the location of the flue tube 18 per the desires of the surgeon during operation. Also shown is an electrical cable 26 for providing power to the apparatus or providing switching connections.

The ultrasonic horn 14 is disposed within the flue 16. During operation of the ultrasonic apparatus 10, irrigation fluid is supplied through the opening 17 into the flue 16. Flue 16 and the ultrasonic horn 14 define an annular cavity 36 therebetween. Irrigation fluid is supplied from flue 16 through cavity 36 to the distal end of the ultrasonic horn 14. A transverse bore is formed in preaspiration holes 115 near the distal end of the ultrasonic horn 14 and communicates with the throughbore 114. The irrigation fluid is drawn from preaspiration holes and the surgical site through inlet 31 into the throughbore 114 along with fragmented tissue, blood, etc., and is removed from the surgical site via the throughbore 114 and the aspiration tube 24. The transverse bore provides an alternate route for fluid to enter throughbore 114 when inlet 31 becomes clogged.

Figure 7:
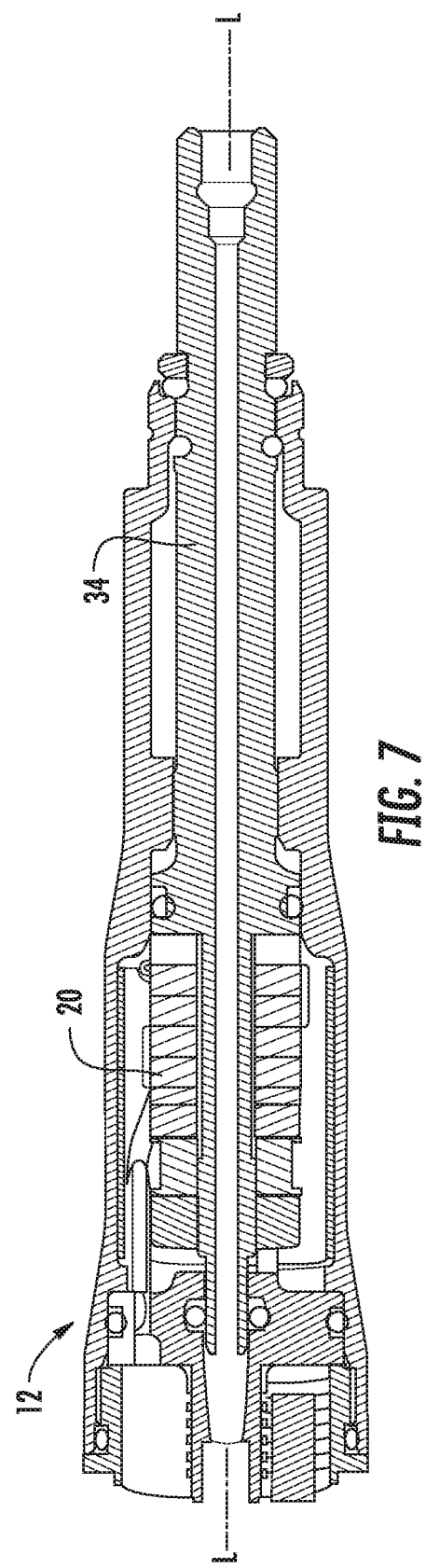
FIG. 7 is a longitudinal-sectional view of a handpiece in accordance with various implementations.

Elements contained in the handpiece 12 are shown in FIGS. 6-7. The transducer stack assembly 100 includes piezoelectric ceramic disks 20 and an internal horn 34. According to various implementations, output generated by an integral piezoelectric ceramic force sensing element (sense ceramic) of the piezoelectric ceramic disks 20 is utilized in separating of surgical tip stroke and power control. For example, and as described herein, output from the piezoelectric ceramic force sensing element can be utilized in generating a feedback based reference drive signal that can be modified according to pulse width modulation and/or amplitude modulation parameters of a selected tissue selectivity level. The separation of surgical tip stroke and power control can advantageously limit power and thermal rise to the surgical site, and/or advantageously control propensity for cavitation in preserving viscoelastic collagen rich tissue, such as bile ducts, arteries, and veins in liver or general surgery, and blood carrying vessels and membranes of critical anatomy in neurosurgery.

The sense ceramic of the piezoelectric ceramic disks 20 provides a voltage proportional to stress, or charge proportional to deflection, thereby enabling monitoring of the stress directly related to surgical tip motion in the tightly coupled resonant transducer horn-surgical tip system. As described herein, output from the sense ceramic (e.g., a voltage output) can indicate such stress, and can be utilized to generate a feedback based reference drive signal that can be modified according to pulse width modulation and/or amplitude modulation parameters of a selected tissue selectivity level—which can enable separating stroke and power control, which is beneficial to tissue selectivity.

The sense ceramic, and control of the drive signal based on output from the sense ceramic and other considerations described herein, can afford amplitude control to greater precision and linearity, essentially 5% increments or finer settings compared to 10% or greater increments of prior art systems. Also, the amplitude control and linearity was poor below 50% in prior art systems; for example, a 10% amplitude setting was found to be about 20% stroke amplitude of the full scale value. Additionally, the control of reserve power with tissue selectivity setting of the prior art systems did not function correctly at low amplitude settings. Implementations disclosed herein employ the sense ceramic with control of commanded stroke look-up tables creating precise wave shapes of outputs that are both pulse width and amplitude modulated. These and other implementations enable reserve power to be controlled at low amplitudes and tissue selectivity to be accommodated at low amplitudes. This can result, for example, from creating a propensity for control of a cavitation threshold according to various implementations disclosed herein.

The piezoelectric sense ceramic provides a voltage proportional to stress, or charge proportional to deflection, thereby enabling a measurement directly related to stroke of the surgical tip and improved linearity and incremental stroke control. The novel approach of using the sense ceramic to monitor stress (force sensing) or deflection coupled with the digital control loop and lookup tables simultaneous controlling pulse width and amplitude modulation corrected limitations on improved selectivity at low amplitudes. This can result in, for example, quantitatively an improvement to 5% increments versus 10% increments in stroke control, and control to a minimum of 5% amplitude with linearity, where the CUSA Excel system had inferior linearity (e.g., 20% output at a 10% setting). Quantitative graphs of tissue selectivity show well behaved data to low amplitude, where CUSA Excel system did not function correctly below about 40% amplitude.

Some fundamental discoveries made by the inventors lead to the innovation of use of the force sense ceramic and microprocessor based control systems with simultaneous pulse-width and amplitude-modulation, with wave shaping and selectivity mapping in view of tissue selectivity. The elements and discoveries related to force sense ceramic and enhanced tissue selectivity are described below and elsewhere herein.

Efficacy in removal of tissue is related to fragmentation power, which is given by power equal to velocity (amplitude multiplied times angular frequency) squared. At a given frequency of resonance of a surgical tip, fragmentation power goes with stroke squared. It evolved in practice that a reduced duty cycle and limited power could also preserve vessels in applications requiring high removal rate, consequently, relative high stroke. An example where this utility became the standard of care is in liver surgery, where the matrix tissue must be removed rapidly to reduce blood loss, while exposing vessels that must be sealed or relatively large veins, arteries, and bile ducts.

Inherent tissue selectivity is adapted to practices where softer tissue of higher fluid content is selectively removed while preserving more collagen and elastin rich vessels and a clear need for limiting power for thermal management, either by surgeon minimally loading the surgical tip or by governing power available for electrical to mechanical conversion. Less was known about the actual response of more elastic tissue and preservation of vessels with limitation of reserve power, duty cycle, and repetition rate.

Implementations described herein evolved from the observation that when tissue progresses to emulsification under high stroke and availability of liquid for cavitation, the tissue is rapidly fragmented and aspirated. More particularly, implementations evolved from the observation that calculated pressure for a given velocity of a surgical tip is directly related to a near vaporization point of liquid, such as saline, or water. Saline is available at the surgical tip as irrigation liquid and soft tissue and blood contain water.

The calculated pressure at onset of profuse cavitation is about the same for two different transducers having about 55% difference in frequency (23 kHz and 35.75 kHz), having 37% difference in surgical tip strokes (266 micrometers @ 23 kHz and 167 micrometers @ 35.75 kHz), and having surgical tips with different surface areas. For example, such two transducers of markedly different frequency with surgical tips (horns) of substantially different stroke, yield similar calculated pressure about 1 ATM (101.3 kPa), based on power transduced, area, and velocity of the horn.

Implementations disclosed herein are further based on the observation that amplitude modulation of a pulse width modulated or otherwise periodically interrupted waveform of a drive signal can limit the number of cycles of tip stroke that are above a cavitation threshold. More particularly, implementations disclosed herein are further based on the observation that the propensity for profuse cavitation is decreased by limiting the number of cycles above the cavitation threshold. For example, various implementations can modulate the amplitude of the commanded feedback signal to control the drive vibration amplitude in accordance with a selected tissue selectivity level, to thereby mitigate the number of occurrences of stroke, of a surgical tip, that are above a cavitation threshold. In some of those various implementations, the amplitude of the drive vibration can be variably modulated over time, where the variable modulation is dependent on the selected tissue selectivity level. For example, the modulation can be varied based on amplitude modulation parameters stored, e.g., in a lookup table in memory, in association with the selected tissue selectivity level. For instance, a sequence of X amplitude modulation parameters can be stored for a given tissue selectivity level, where each amplitude modulation parameter indicates how the amplitude should be modulated during a corresponding time period. X can be a number greater than three (3), such as a number that is equal to the number of milliseconds in a cycle time for the given tissue selectivity level (e.g., X=50 for a 50 ms cycle time). The sequence of amplitude modulation parameters can be cycled back through when the end of the sequence is reached. At each control cycle of generating the drive signal to be provided for driving drive ceramic(s) of a surgical device, the corresponding amplitude modulation parameter can be utilized to determine the amplitude of the commanded feedback amplitude for that control cycle. As one particular instance, the amplitude modulation parameter can indicate a percentage by which a commanded feedback amplitude should be reduced, and the feedback controls the drive signal necessary to control the amplitude of vibration of the drive ceramic(s) of the surgical device. As described herein, in addition to different amplitude modulation parameters being utilized for each of a plurality of different tissue selectivity levels, a different cycle time and duty cycle can also be utilized for each of the plurality of different tissue selectivity levels. The different cycle times and duty cycles can likewise each be stored, e.g., in a lookup table in memory, in association with their corresponding selected tissue selectivity level.

The tissue selectivity settings of the controller and user interface were mapped to the physical response favored by surgeons. It was determined that the settings could be mapped to no selectivity or standard setting, low, medium, and high tissue selectivity. The translation of these settings is in the form of the amplitude command output look-up table. The command causes a modulation of the output stroke as a function of time. The PID (Proportional to Integral and Derivative) control loop forces the stroke to match the commanded levels via error signals multiplying the input to the frequency generator and power amplifier. The settings are mapped such that the first setting provides a degree of selectivity change that is noticed by the surgeon, and the next may be discernable, and the next certainly discernable, and the last highly discernable.

It is observed that the surgeon should have a rate of removal that is practical, and a tissue selectivity response at that rate of removal supports the practice. As an example, the surgeon needs to be able to remove the matrix of the liver fast enough to prevent the patient from having excessive blood loss while preserving the vessels, bile ducts, veins, and arteries for sealing. Given capability of adjusting the amplitude in 5% increments over a range of use coupled with multiple (e.g., 4) selectivity settings at each increment, it is found that one can accomplish the range of response necessary. The surgeon can set from minimal selectivity to a selectivity exceeding the need of their practice. They have the capability of settings that take tissue and enhance selectivity. In practice, if the surgeon dwelled on the vessel or viscoelastic membrane for an extended period or provide greater pressure, they could compromise the vessel or membrane. Implementations described herein enable the inherent selectivity over a broader practical range, and enable exceeding the preservation time typical of the fragmentation rate.

Testing shows a surgeon could uniquely remove tissue from vessels in the liver to a greater degree than they would typically use or need in a bleeding liver. Surgeons could take tissue from one gyrus of the brain, such as would be done in Glioma tumor removal, while preserving the pia separating the next gyrus. Selectivity capable of preserving the next pia is paramount to the surgeon. It was determined that high sensitive settings at low amplitude could even differential gray and white mater, such that the gray matter was removed and the white mater appeared elastic to the ultrasonic aspirator. The surgeons appeared to have the full range on necessary selectivity for their practice following iterative adjustment and mapping of the wave packets.

According to various implementations, a greater degree of control in the ultrasonic aspirators in response to viscoelastic tissue such as vessels and membranes is enabled by the capability of tissue selectivity with the improved control system via the force sense ceramic, real time control of amplitude, the improved implementation of repeatable simultaneous pulse width and amplitude modulation, wave shaping with capability of a look-up table to adjust the number of cycles of amplitude above a given cavitation threshold, and/or systematically mapping the wave packet to influence the propensity to cavitation in saline irrigation liquid and tissue.

Figure 8:
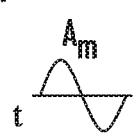
FIG. 8 illustrates some equations that may be relevant to various implementations.

Referring now to FIG. 8, some equations are illustrated that demonstrate a derivation of fragmentation power based on physical principles. Maintaining tip stroke at a given frequency is desirable for efficacy. Reducing tip stroke could actually cause more heating due to less efficient tissue removal. The tip stroke can be maintained while the power behind the stroke is limited to limit transduction of power to the surgical site. The equations of FIG. 8 are supported generally by performing removal rate studies of bovine tissue in statistical studies where the amplitude is halved, for example.

As mentioned above, the calculated pressure of onset of cavitation in saline and water for two different transducers of greatly different frequencies with surgical tips of greatly different stroke, and devices of different area, indicate similar cavitation threshold at negative atmosphere. For example, two transducers of markedly different frequency (CUSA Excel 36 kHz Extended MicroTip and CUSA Excel 23 kHz Standard Tip) with surgical tips (horns) of substantially different stroke, yield similar calculated pressure of about 1 ATM (101.3 kPa), based on power transduced, area, and velocity of the horn. This is demonstrated in FIG. 9. The calculated pressure at given velocity of the surgical tips of different frequency are shown along with simple observation of the 23 kHz Standard Tip often utilized in liver surgery. The amplitude of the surgical tip also decreases with selectivity setting, in this case selectivity increasing with the number of plus symbols shown. The propensity to cavitation onset in saline decreases with selectivity setting, owing to lower amplitude and fewer cycles at the amplitude occurring in each wave packet.

Figure 10:
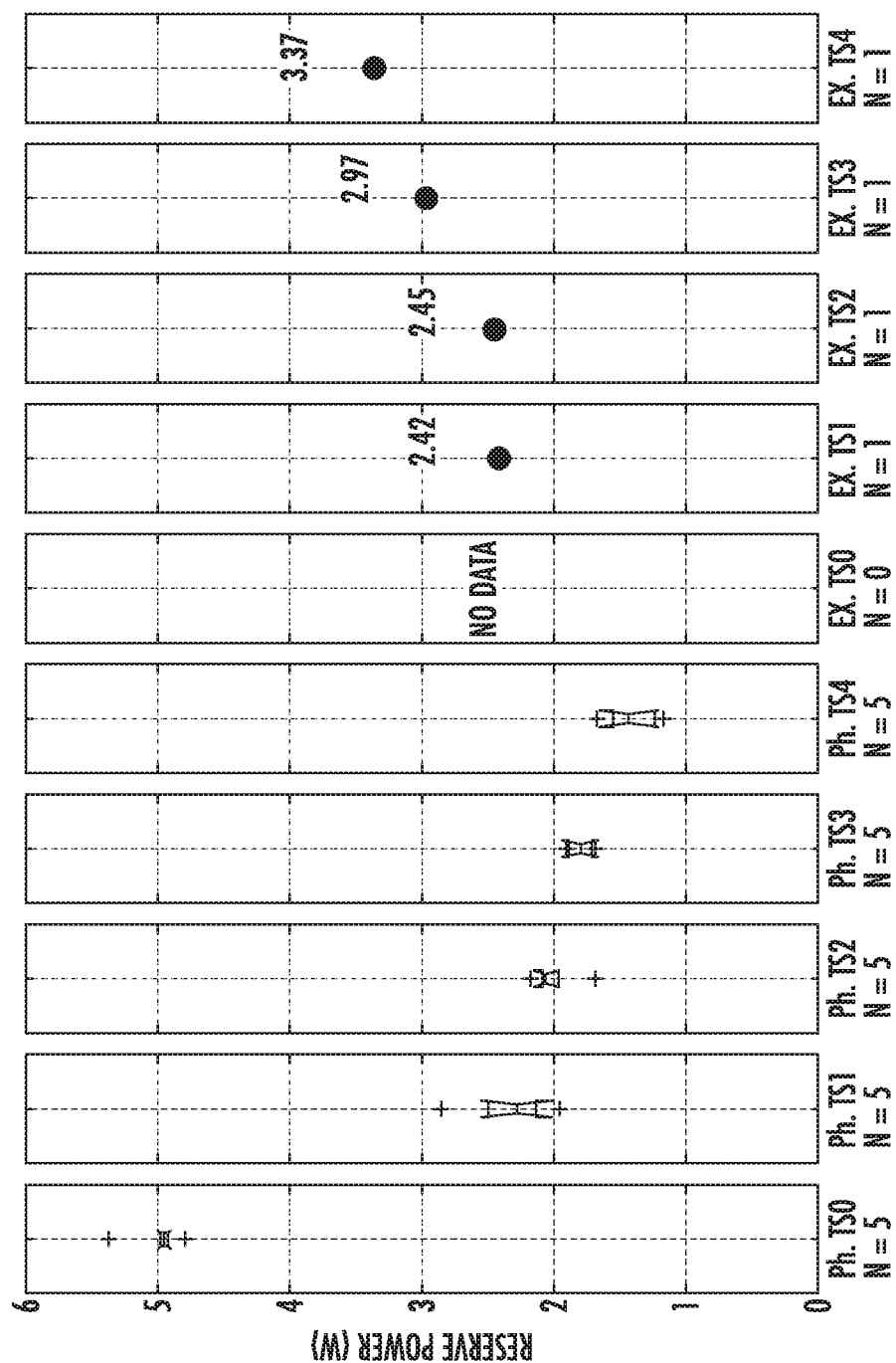
FIG. 10 is a reserve power comparison between the system in accordance with various present implementations (Ph) and a prior art system on the market (EX)
Figure 12:
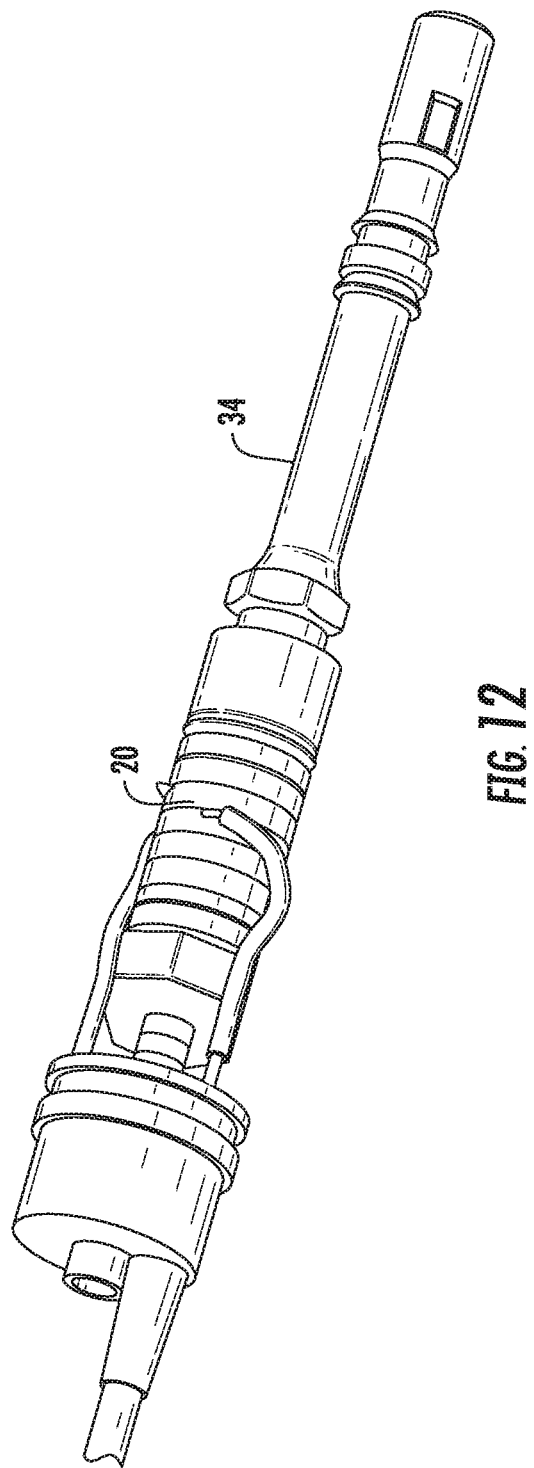
FIG. 12 is a perspective view of handpiece internal elements including a transducer stack assembly in accordance with various implementations.
Figure 13:
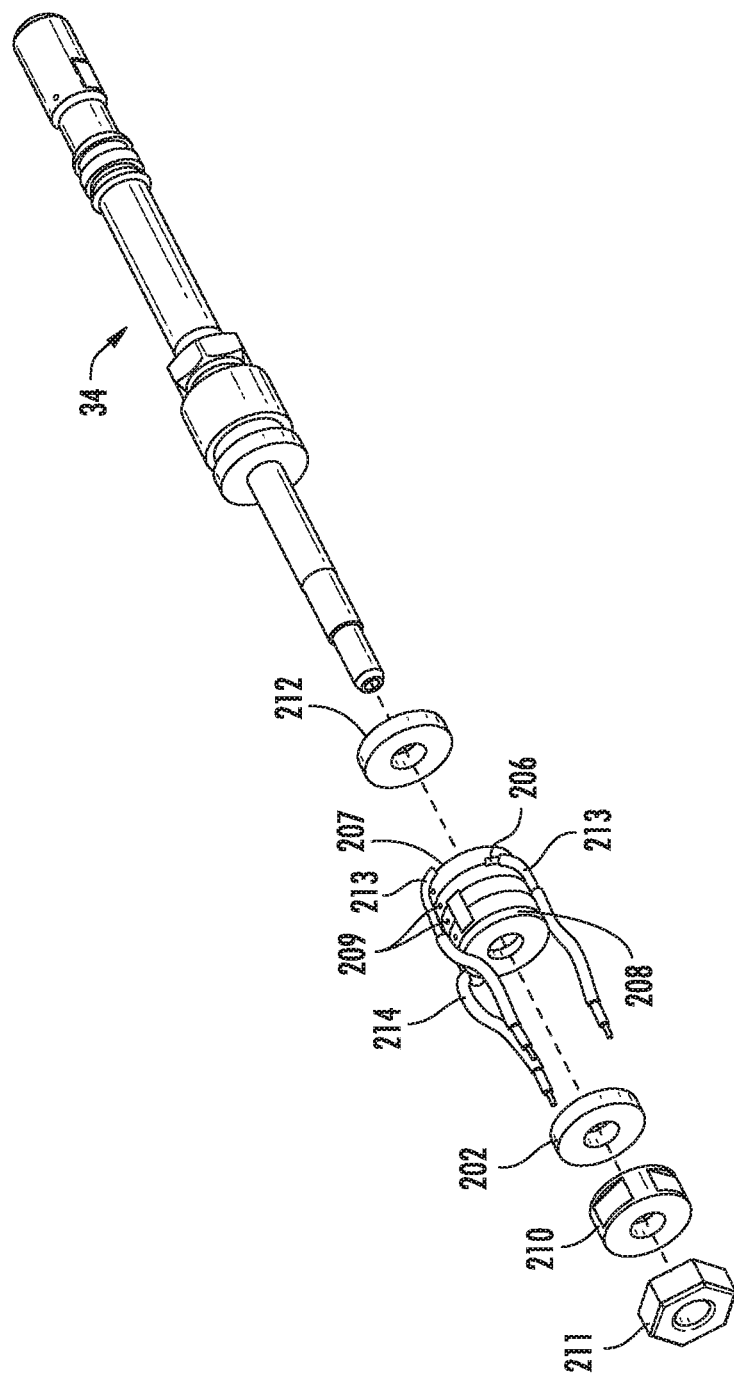
FIG. 13 is an exploded view of the transducer stack assembly shown in FIG. 12.
Figure 14:
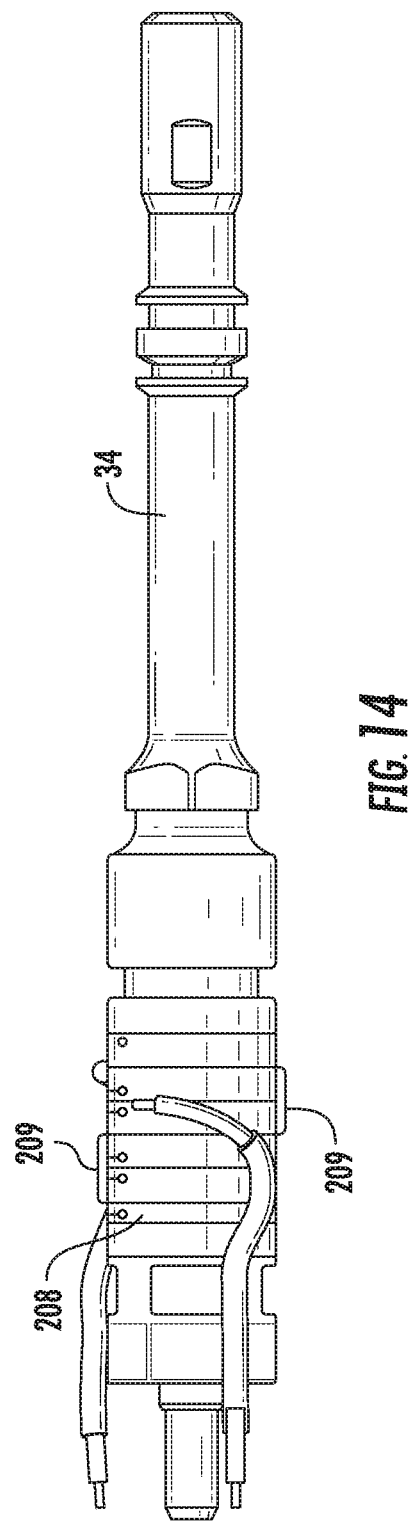
FIG. 14 is a side view of a transducer stack assembly of FIG. 13.
Figure 15:
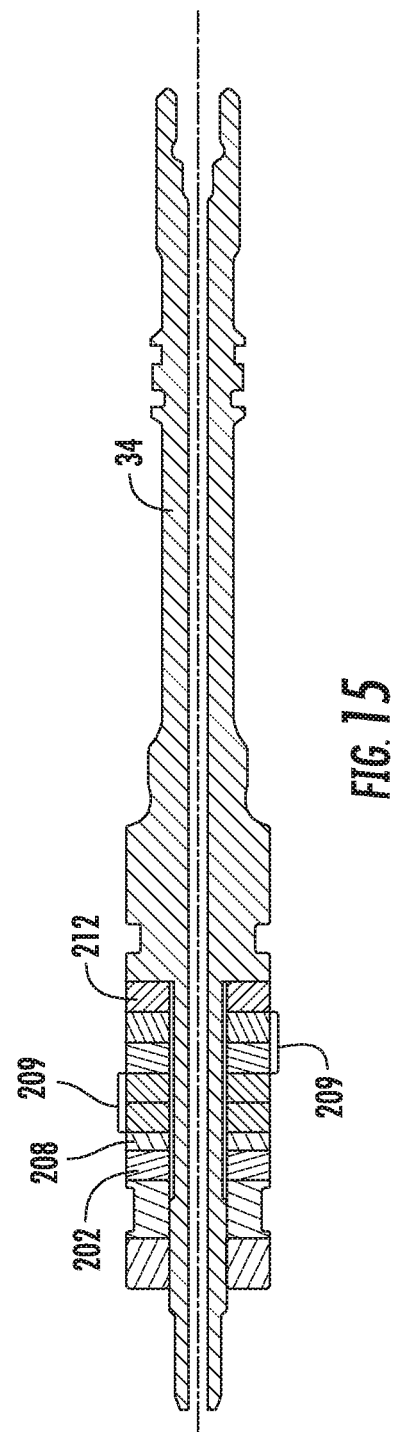
FIG. 15 is a longitudinal-sectional view of the transducer stack assembly of FIG. 13.
Figure 16:
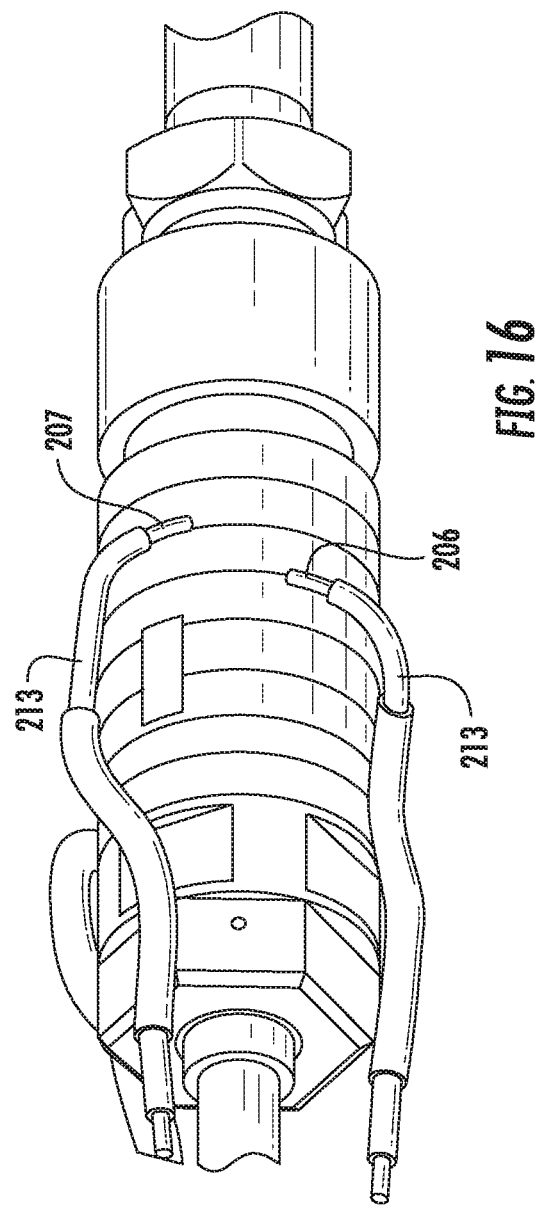
FIG. 16 is a perspective view of a proximal portion of the transducer stack assembly of FIG. 13.

The force sense ceramic was incorporated into a piezoelectric stack transducer with the new controller, labeled in FIG. 10 as "Ph". It is compared to the CUSA Excel system at 20% amplitude, labeled in FIG. 10 as "EX". The improved characteristic of controlled reserve power is shown in FIG. 10.

Characteristic waveforms are shown, exhibiting a duty cycle such as CUSA Excel system, with a high and low amplitude transition. The wave packet can be tailored via a lookup table in firmware within the control loop cycle. The amplitude can be set by a lookup table as commanded stroke levels. Excel had some characteristic modulation due to inertia of the system and active response of the transducer and surgical tip. Here, the amplitude can be precisely replicated and adjusted for each selectivity setting. These wave shapes were mapped to standard, low, medium and high selectivity tested with the surgeons. The result is a well behaved system with increase selectivity even at low amplitude settings. There is statistical variation in measured data, primarily due to the measurement techniques, as the system clock output, control loop timing, and lookup table are exactly repeatable, to the precision of the control loop operation.

The amplitude output is shown in FIG. 11 to have fewer cycles above a threshold, and this slope can be adjusted. It shows lower reserve power due to reduced duty cycle, marginally lower maximum amplitude, much smaller fraction of cycles at peak amplitude, and not simply pulse width modulation. Amplitude maximum exists for extended cycles, but average or RMS levels would be much lower. It is believed that this characteristic wave shape and number of cycles above a cavitation threshold may have always played some role in response of tissue even to the analog systems. However, implementation is greatly improved with the digital control loop and programmed lookup table outputs.

The original systems were capable of control the ultrasonic aspirator selectivity, and this became the standard of care in liver surgery at higher amplitudes of operation, e.g., 70%-100%. The present disclosure has extended this utility to lower amplitudes that will be useful in, for example, neurosurgery. Tissue selectivity is increasing with plus increases, such that more vessels are preserved. These vessels would be sealed, and the lobe containing the tumor would be removed. Finer dissection with high selectivity of the new transducer and control systems enables the surgeon to finely clean a large vessel of all tissue.

Some practical implementations will be described using a 36 kHz transducer. The handpiece incorporates the transducer within the housing. The surgical tip is attached to the transducer and amplifies motion greatly with stepped and specialty horns. Irrigation liquid is supplied via a polymer flue surrounding the surgical tip. Effluent and fragmented tissue is suctioned under vacuum through the central channel of the surgical tip and transducer.

As shown in FIGS. 12 to 16, the force sense ceramic (also referred to as the feedback ceramic) 208, power drive ceramics 209, and insulating ceramics 202, 212 are put under high compressive stress, to about 45 MPa. This is done so that the drive power piezoelectric ceramics do not go in to tension, such that they fail mechanically. Power drive ceramics 209 replenish power lost from the resonating stack and surgical tip. The motion of the drive ceramics 209 is slight relative to the motion of the stepped internal horn 34 and surgical tip, where motion of the stack is about 2.5 micrometers and motion of the surgical tip can be 183 micrometers peak-to-peak. The transducer stack assembly 100 includes other elements such as electrodes 206, 207, a spacer 210, a nut 211, wires 213 such as silver plated copper wires with silicone rubber jacket, and heat shrink tubing 214.

The handpiece cable is assembled along with an EEProm (Electronic Erasable Programmable Memory) chip, and Lemo connector. The EEProm chip stores a scale factor for surgical tip stroke unique to the transducer that is calibrated in manufacturing.

The control system related to handpiece functionality is described below. The handpiece usually works with the ultrasonic controller generator.

1. Hardware

Figure 17:
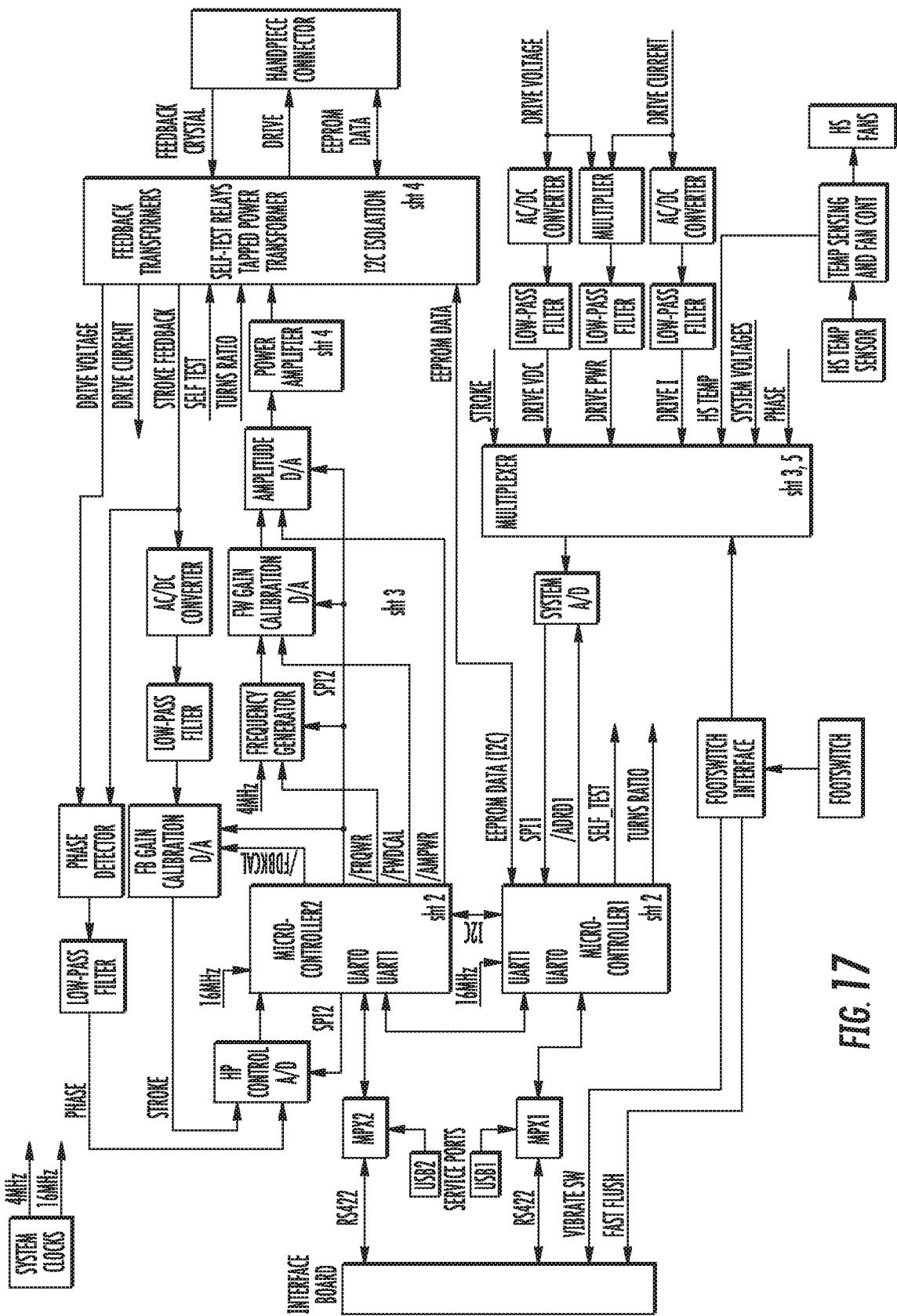
FIG. 17 illustrates a schematic diagram of components, and interactions between the components, in accordance with various implementations.

In some implementations, an ultrasonic control board forms part of the tissue ablation system. Its purpose is to control ultrasonic power to a piezoelectric handpiece. The ultrasonic controller board is broadly based on the CUSA® NXT Ultrasonic Controller Board (Integra LifeSciences Corporation, Plainsboro, N.J.). One difference between the boards is the adoption of a voltage motional feedback system rather than a motional bridge. Additionally two microcontrollers are used. One controls general housekeeping tasks while the other is dedicated to controlling phase and stroke in order to achieve a faster response time, resulting in faster control. FIG. 17 provides an overview of the circuit function.

Figure 18:
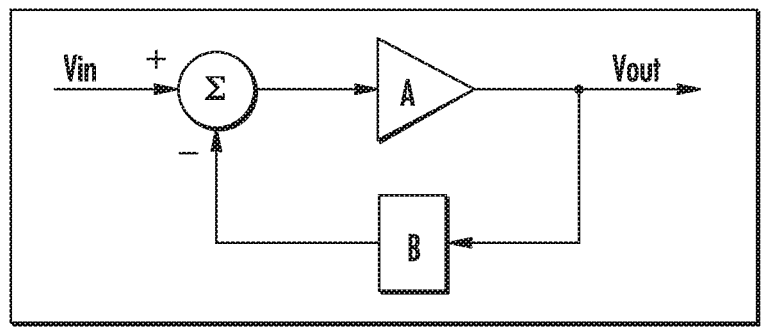
FIG. 18 illustrates a schematic diagram of an example closed loop control system.

The ultrasonic control board controls ultrasonic power to a piezoelectric handpiece by monitoring demand from the host and controlling the stroke by feedback from a piezoelectric feedback ceramic. The feedback circuit monitors the stroke from the feedback ceramic and tries to maintain the stroke by adjusting the drive to the main ceramic stack, the feedback can be controlled, for example, in firmware. A standard transfer function for any control system can be applied to the closed loop controller system. See a closed loop control system illustrated in FIG. 18 and the description below.

$$G = \frac{A}{1 + AB}$$

Where A is forward gain and B is feedback gain. As A grows larger, G approaches 1/B; the system then is relatively insensitive to the value of A. Forward gain includes proportional and integral terms. The integral term can be considered to be infinite gain at 0 Hz; therefore there is no static error. These can be implemented in the handpiece control microcontroller firmware.

The system is designed to control piezoelectric transducers having feedback crystal in the 20 to 40 kHz range.

The control system can consist of two loops. The primary loop controls the phase relationship between the drive voltage and the stroke feedback by adjusting the frequency. This can be needed as the handpiece and tip form a high-Q, sharply resonant element. Response drops off rapidly with deviation from resonance. The second control loop adjusts the forward gain in order to maintain stroke.

2. Software-Firmware Ultrasonics

This firmware runs on the two microcontrollers on the ultrasonics board and controls the handpiece. The firmware on Microcontroller 1 (referred to as the Monitor micro) reads in the control parameters from the handpiece EEPROM and responds to messages from the console software which instructs it to set operating parameters and enter and leave the appropriate operating mode. This firmware interfaces with the firmware on the second microcontroller (referred to as the control micro) which runs the control loop necessary to control the handpiece.

3. Run Mode (1) Poll Handpiece connection to see if the handpiece is disconnected. If so, reset the handpiece parameters and return to Idle Mode.

(2) Poll the footswitch connection to see if the footswitch (and/or other user interface element) is disconnected. If so, return to Idle Mode.

(3) Activate the power amplifier by waking it up from sleep mode (4) When the footswitch is not pressed, the firmware writes out "0" to the amplitude D/A to reset the drive voltage to the handpiece to zero. It also puts the power amplifier in sleep mode.

(5) On every footswitch press (and/or other user interface input), the control micro firmware activates the power amplifier (i.e. disables sleep mode). On the first footswitch press after a handpiece has been connected, the firmware will attempt a frequency sweep if it has not been performed already via the handpiece test. It then runs the closed-loop PID control loop to drive the handpiece at the commanded amplitude. During the handpiece control process, the firmware will read and adjust the phase/frequency, followed by adjustment of control amplitude, to drive the handpiece. This operation is related to the timing execution of the loop.

(6) Sends the status of the run mode operation (resonant frequency, current operating frequency feedback amplitude, etc.) periodically (and/or at other non-periodic interval(s)) to the Monitor micro via a W message. If there are any error conditions at any stage, return to Idle mode and report the error code to the console software.

As described earlier, the effective requested amplitude in D/A counts is determined on the monitor micro and passed on the control micro along with the specified tissue selectivity level. The tissue selectivity level is used in determining what the effective amplitude ("demand") is for the current step of the control loop.

4. Tissue Selection Feature

The tissue selection feature has multiple selectable tissue selectivity levels. For example, it can have five (5) possible levels, numbered 0 to 4 (corresponding from Off to Maximum in the console software). Depending on the level of the tissue selection feature, the requested amplitude from the monitor micro is modulated by a waveform specified for that tissue selectivity level (see table and graphs below). This resulting modulated amplitude is applied to the handpiece drive signal reducing the effective power available to the surgeon for fine control of the tissue ablation. The default value of the tissue selection feature is 0: no table is used;

amplitude is always set to the requested value from the monitor micro, i.e. the tissue selection feature is effectively turned off.

The look-up tables used to generate the tissue selectivity values for tissue selectivity settings Low through Maximum are hardcoded in the firmware as shown below.

| Setting | Waveform Duty Cycle (ON indicates amplitude modulation, OFF indicates amplitude unchanged) | Waveform Values (Multipliers) (Multiplier of 64 indicates "OFF" state - amplitude unchanged from requested amplitude level) |
| --- | --- | --- |
| OFF (Standard) | continuously ON | Unchanged from requested amplitude |
| LOW | 50 ms cycle time: 40 ms ON, 10 ms OFF | 64, 58, 53, 47, 43, 37, 32, 28, 24, 21, 19, 17, 17, 17, 18, 19, 21, 22, 25, 27, 31, 34, 38, 42, 45, 48, 50, 52, 54, 56, 57, 58, 59, 60, 61, 62, 63, 64, 64, 64, 64, 64, 64, 64, 64, 64, 64, 64, 64, 64 |
| MEDIUM | 40 ms cycle time: 30 ms ON, 10 ms OFF | 64, 58, 53, 47, 43, 37, 32, 28 ,24, 21, 19, 17, 17, 17, 18, 19, 21, 22, 25, 27, 31, 34, 38, 42, 45, 48, 50, 52, 54, 56, 57, 58, 59, 60, 61, 62, 63, 64, 64, 64 |
| HIGH | 30 ms cycle time: 20 ms ON, 10 ms OFF | 58, 53, 47, 43, 37, 32, 28, 24, 21, 19, 17, 17, 17, 18, 19, 21, 22, 25, 27, 31, 34, 38, 42, 45, 48, 50, 52, 54, 56, 57 |
| MAXIMUM | 20 ms cycle time: 10 ms ON, 10 ms OFF | 43, 37, 32, 28, 24, 21, 19, 17, 17, 17, 18, 19, 21, 22, 25, 27, 31, 34, 38, 42 |

For tissue selectivity values other than Off, amplitude demand can be calculated by using one of four look-up tables of percentages. Each look-up table describes the waveform for a given tissue selectivity setting. In each look-up table, 100% is represented as 64, in order to facilitate binary arithmetic (see Column 3 in the table). Each entry in the look-up table is specified at an interval of 1 millisecond. Therefore, if the control loop is running at a faster rate, the current modulation value in the look-up table is effectively repeated until the 1 ms interval is completed. For instance, if the control micro firmware loop runs at a speed of 500 microseconds (0.5 milliseconds), each value in the look-up table will be used for two steps of the loop before moving on to the next entry. The requested amplitude is multiplied by the table entry and then divided by 64, so the amplitude varies with time in the desired waveform. A waveform index is used to keep track of the current position in the waveform. This index varies from 0 through the size of the waveform table (minus 1) and is incremented on each 1 millisecond increment (or recycled back to zero when the end of the waveform table is reached). The index is also reset whenever the tissue selectivity setting is changed or when tip vibration is halted.

Figure 19A:
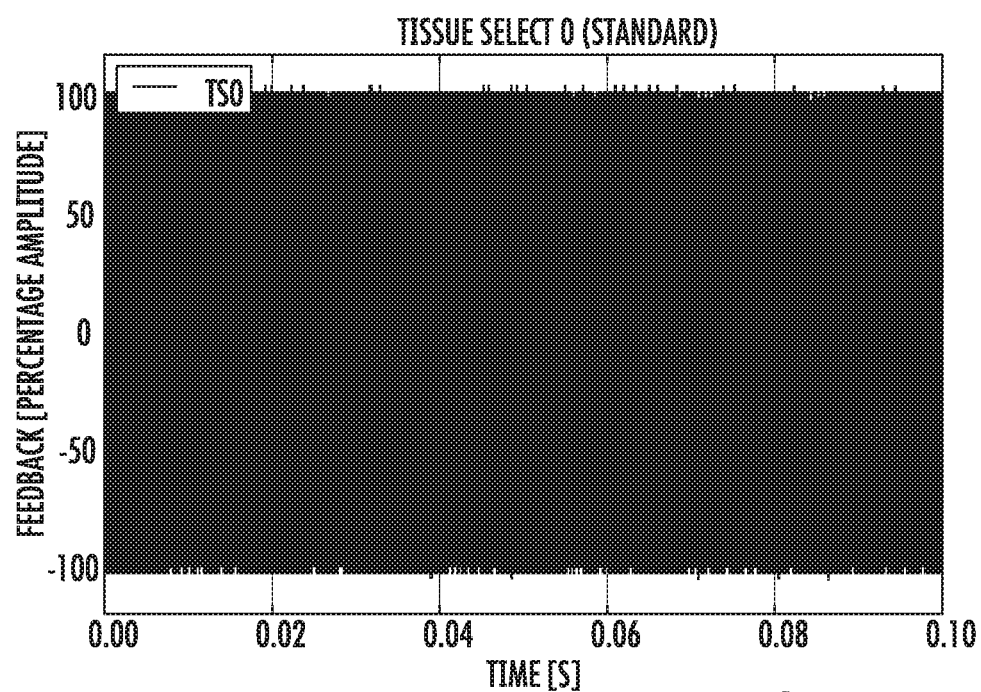
FIGS. 19 A-E show sample waveforms that correspond to each of a plurality of example tissue selectivity values (Levels 0 through 4) in accordance with various implementations.
Figure 19B:
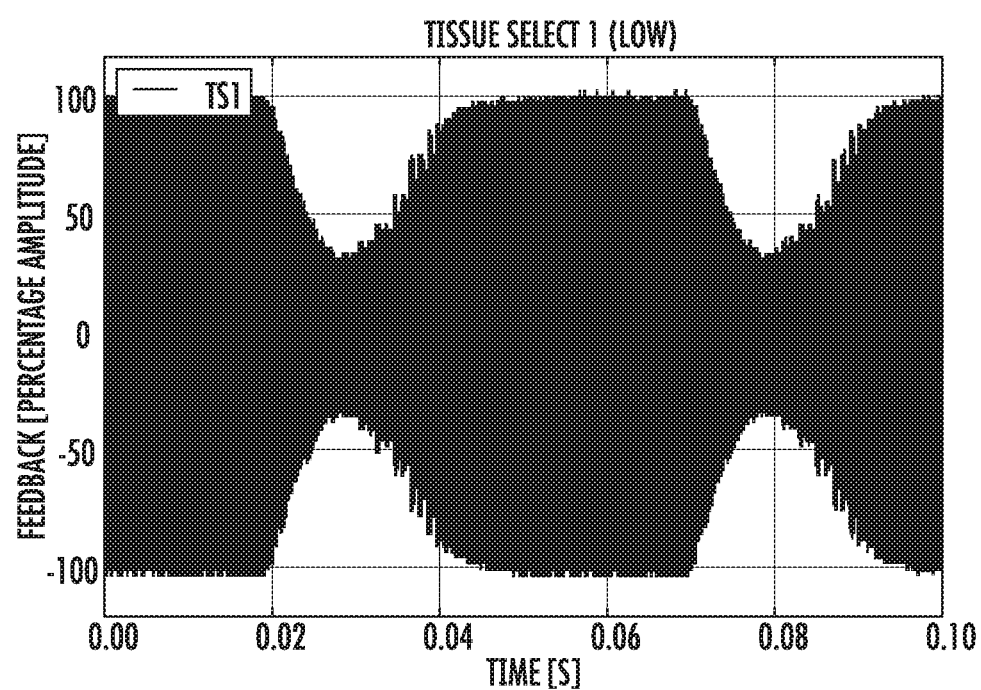
Figure 19C:
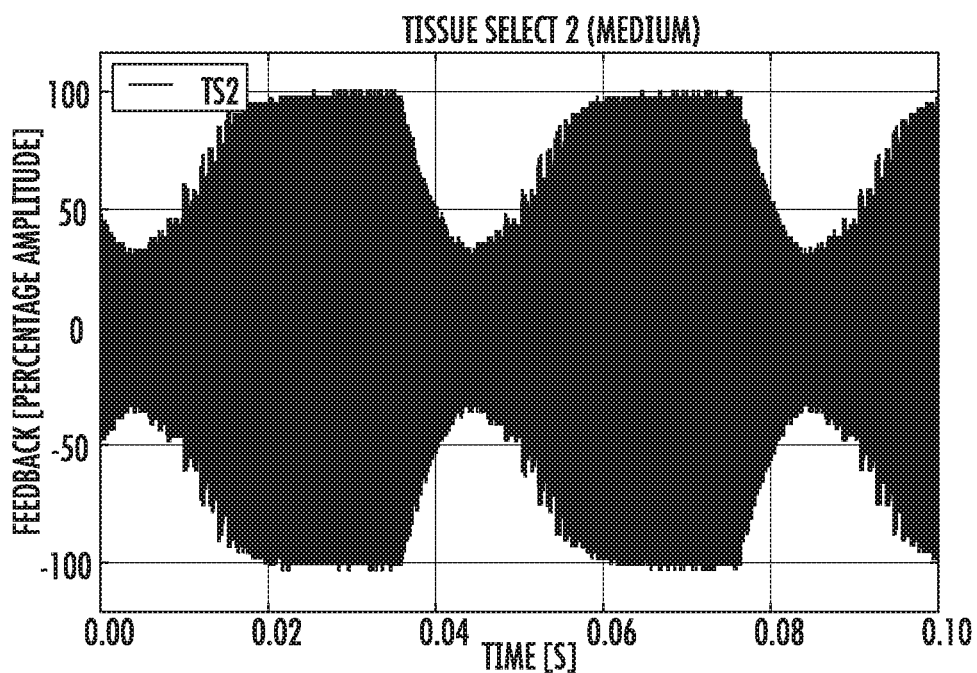
Figure 19D:
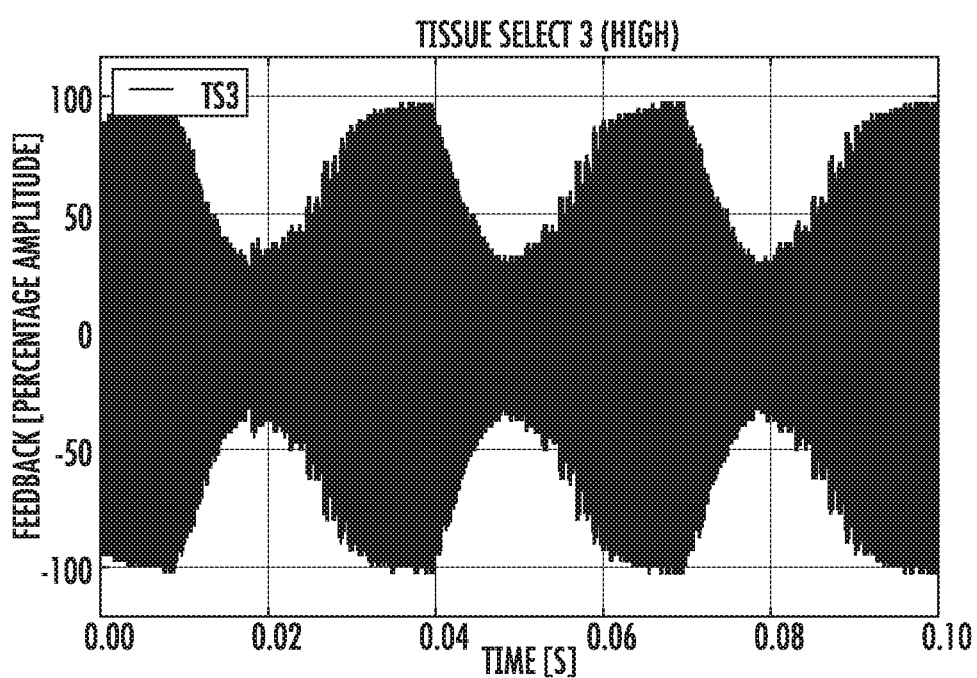
Figure 19E:
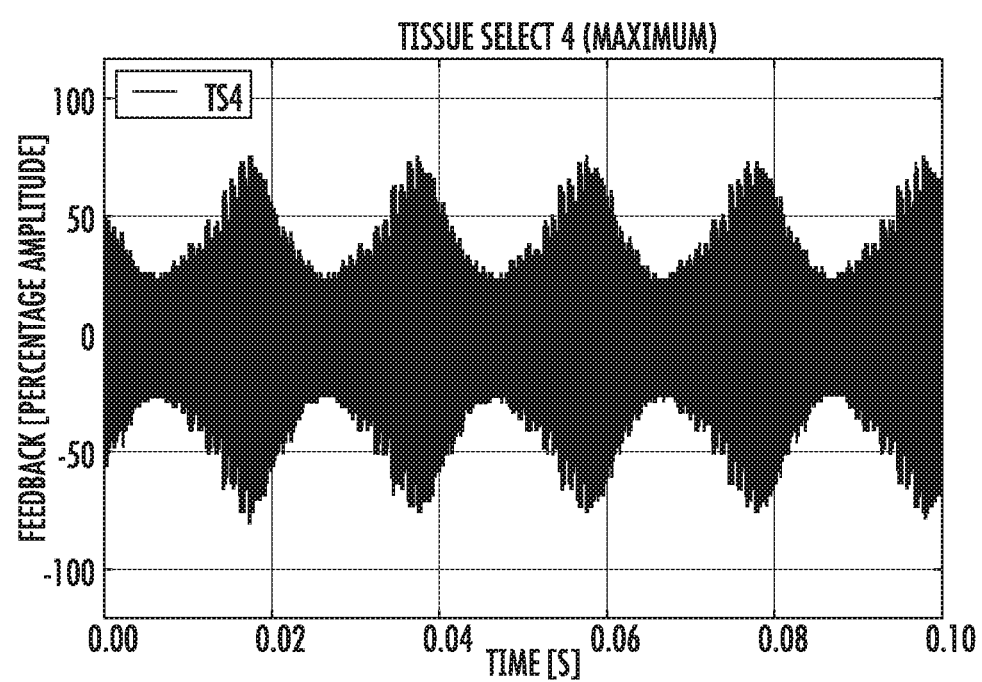

When operating in the tissue selection mode (from Level 1 through Level 4), the control micro firmware returns the scaled value corresponding to the peak of the last completed waveform (for Tissue Selectivity values 1-4) as shown in FIGS. 19A-E. As shown in FIG. 19A, for Tissue Selectivity 0, the firmware returns the most recent feedback amplitude. This value constitutes the feedback amplitude send by the monitor micro to the console software as part of a C message. FIGS. 19B-E show the sample waveforms that correspond to each Tissue Selectivity value from Low to Maximum (internally denoted in the firmware as Levels 1 through 4).

The implementation of tissue selectivity on the digital control loop platform is readily understood by viewing the waveforms and descriptions. Look up tables can be provided to construct precisely repeatable wave patterns rather than a simple duty cycle at an on amplitude and off amplitude. The output words on the lookup table are scaled appropriately to the multiplier of the frequency generator input to the power amplifier. There is existing closed-loop control of stroke via the PID loop to the levels commanded. The waveforms are seen to provide different slopes and number of cycles above specific amplitudes. The directly coupled stress or deflection control of stroke with the feedback and look-up table afford a greater degree of accuracy to a response favored by the surgeon, and exact precision or repeatability to the clock of the loop and amplitudes of the look-up table. The system allows the span of extremely high selectivity to practical selectivity, to standard removal for more tenacious tissue.

In use, the tissue selection feature allows the surgeon to maintain a high fragmentation rate while increasing selectivity and control at the surgical site. The feature provides several major benefits. It gives the surgeon greater control and precision when resecting near critical structures, and enhances tissue selectivity while maintaining fragmentation capability. The power to the site is limited while strength and efficacy in tissue removal are still provided. It provides maximum tissue selectivity, and gives surgeon superior tactile feedback Fragmentation occurs when the vibrating tip comes into contact with tissue. As the tip begins to move toward tissue, it accelerates, then impacts and penetrates the tissue. The acceleration, impact, and penetration produce a combination of direct mechanical forces and hydrodynamic pressures that burst cells. Several variables affect the fragmentation rate, and most of the variables are functions of an ultrasonic surgical aspiration system. The first variable is amplitude refers to the tip excursion, which is the total distance the tip travels. Greater amplitude results in greater fragmentation rate. The second variable is aspiration. Aspiration has several functions. It draws tissue toward the vibrating tip and creates constant tissue contact. It removes irrigation and fragmentation debris from the surgical site. If there is no suction or low suction, tissue contact does not occur, resulting in minimal tissue fragmentation and increased tissue temperature. The third variable is tip acceleration, which produces the peak forces and pressures that fragment tissue. The fourth variable is tip cross-sectional area at the tip-tissue contact site. These variables also affect tactile feedback, what the surgeon's hand feels when using the handpiece.

With all other variables remaining constant, the tip does not fragment all tissue types equally effectively. Another variable, tissue strength, affects fragmentation rate. This is referred to as inherent tissue selectivity. "Low strength" soft tissues that are easiest to fragment include the brain and most organs. Older, partially dried tissues are also easy to fragment. "High strength" strong tissues that are most difficult to fragment include vessel structures, tendons, ligaments, healthy skin, and organ capsules. Strength increases and fragmentation rate decreases with tissue containing greater collagen, elastin, or both (collagen type, quantity, and organization affect cell structural quality).

Tissue strength also affects tactile feedback. The surgeon can feel a difference between the tip contacting low strength tissue and the tip contacting high strength tissue. As the tip works through low strength tissue, the surgeon feels a smooth, rhythmic sensation from the handpiece. When the tip contacts high strength tissue, it feels like it is "bouncing off" the tissue. Also, the smooth, rhythmic sensation becomes rougher. To avoid fragmenting high strength tissue, the surgeon must apply less pressure to the tip or move the tip away from the tissue. To continue fragmenting high strength tissue, the surgeon must manually apply more pressure. Continued manual pressure on the footswitch pedals could result in unintentional damage to critical structures. Using the tissue selection feature, the ultrasonic aspirator system can help the surgeon avoid these problems when dissecting near critical structures.

It is possible to increase the inherent selectivity resulting from variations in tissue strength while maintaining amplitude, tip acceleration, and suction. This increase in selectivity results from reducing the adaptive power that drives the tip. The ultrasonic generator delivers electrical power (which is directly related to the acoustic power present at the tip, which results in fragmentation) to the handpiece. The power delivered to the handpiece may be described in three terms: (1) Initial power: the quantity of power necessary to drive the tip vibration in air; that is, no contact with tissue. (2) Adaptive power (also referred to herein as reserve power): the power necessary to maintain tip vibration under load (in contact with tissue). When the tip encounters load, a feedback loop in the system senses the additional load and provides additional power to maintain tip vibration. (3) Maximum power: the greatest power output the console can provide. Maximum power is the sum of initial and adaptive power. The term "adaptive power" and "reserve power" are used interchangeably herein.

There is a common misunderstanding of the amplitude setting. It has been common practice to decrease the amplitude setting when encountering critical structures. The reasoning behind this practice is that the lower amplitude setting results in slower fragmentation rate and greater selectivity, thus greater control to help avoid damage when dissecting near the critical structures. Consider this reasoning more carefully. It is true that decreasing the amplitude setting also decreases the fragmentation rate. It is also true that because the fragmentation rate is slower, the surgeon has a little more time to move the tip away from a critical structure before damaging it; therefore, the surgeon seems to have greater selectivity and control. However, it is incorrect to say the surgeon gains greater selectivity, thus greater control and precision, when dissecting near critical structures. This is because decreasing the amplitude does not greatly affect the adaptive power. In fact, decreasing the amplitude leaves plenty of adaptive power. When the tip contacts critical structures, it still has more than enough power to fragment them if the surgeon applies pressure or prolongs the tip-tissue contact. Therefore, decreasing the amplitude setting gives reduced fragmentation ability, reduced fragmentation rate, little increase in selectivity, and little reduction in adaptive power.

Ultrasonic energy is inherently selective. It fragments soft tissue more easily than collagen-rich tissue. The tissue selection feature is a safety setting that allows the surgeon to increase selectivity and safety without sacrificing procedure speed. The tissue selection function limits power when the tip encounters a blood vessel, providing a wider margin of safety in preserving the vessel.

The tissue selection feature may have several different settings. An example of 5 settings is provided below:

| Level of Selectivity | Fragmentation Rate |
| --- | --- |
| 0 (Off) Default | Maximum Power |
| 1 Low | Slightly decreased tissue removal rate, increased tissue selectivity and tactile feedback |
| 2 Medium | Further decreased tissue removal rate, increased tissue selectivity and tactile feedback |
| 3 High | |
| 4 Maximum | Slowest tissue removal rate, maximum tissue selectivity and tactile feedback |

Under standard operation, power is continuous. The console provides ample adaptive power, as necessary to maintain amplitude under heavy load. Under operation at a high or maximum tissue selectivity setting, both adaptive power and amplitude are reduced. When the tip encounters strong tissue, it will not be fragmented at all due to reduction in amplitude.

Implementations disclosed herein provide finer control at low amplitudes. Tissue selectivity is enhanced at low-amplitudes quantitatively with graphs showing well behaved monotonically decreasing reserve power with increased selectivity settings, where earlier systems could not control tissue selectivity. The force sense ceramic afforded an improvement from 10% increment settings to 5% increment settings. Linearity of the control is improved to amplitude settings as low as 5%, where previously at 10% amplitude setting could yield 20% amplitude output.

Figure 20:
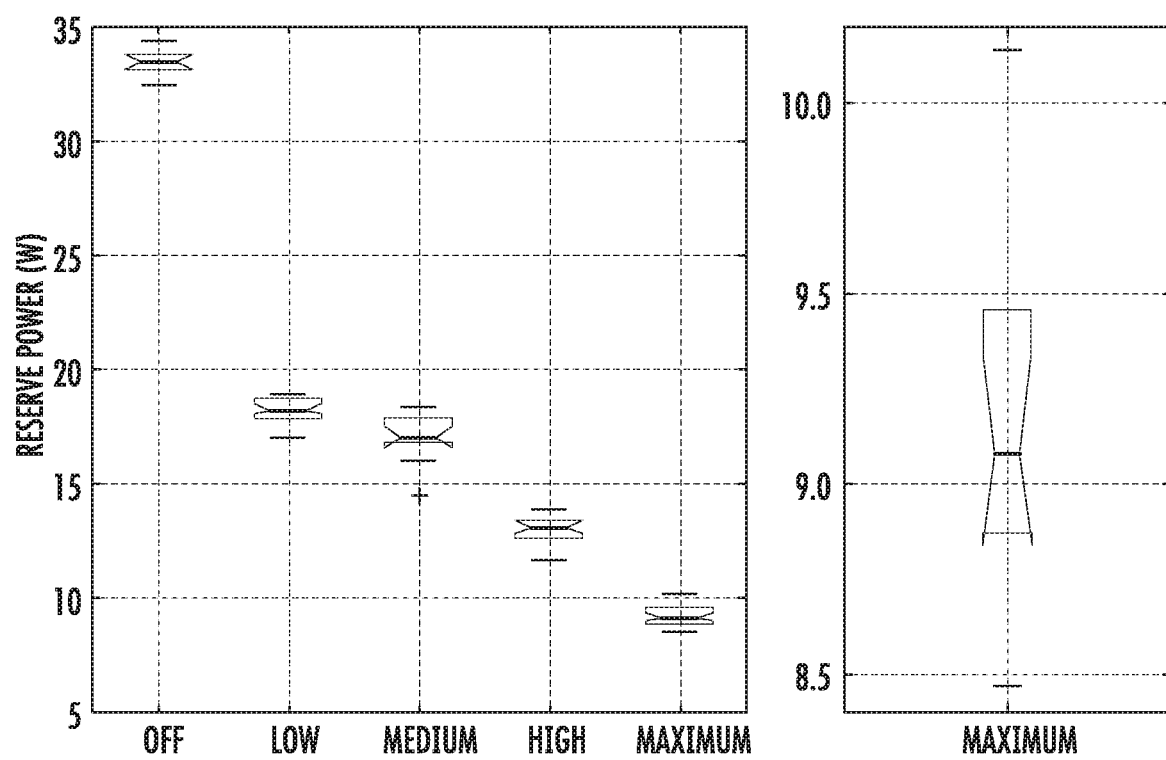

As shown in FIG. 20, performance at full amplitude was preserved while improving control at low amplitudes. The tissue selectivity and fragmentation capability was evaluated at multiple sites following adjustment based on previous testing. Results were very favorable. Surgeon testing clearly showed improved selectivity was achieved.

Figure 21:
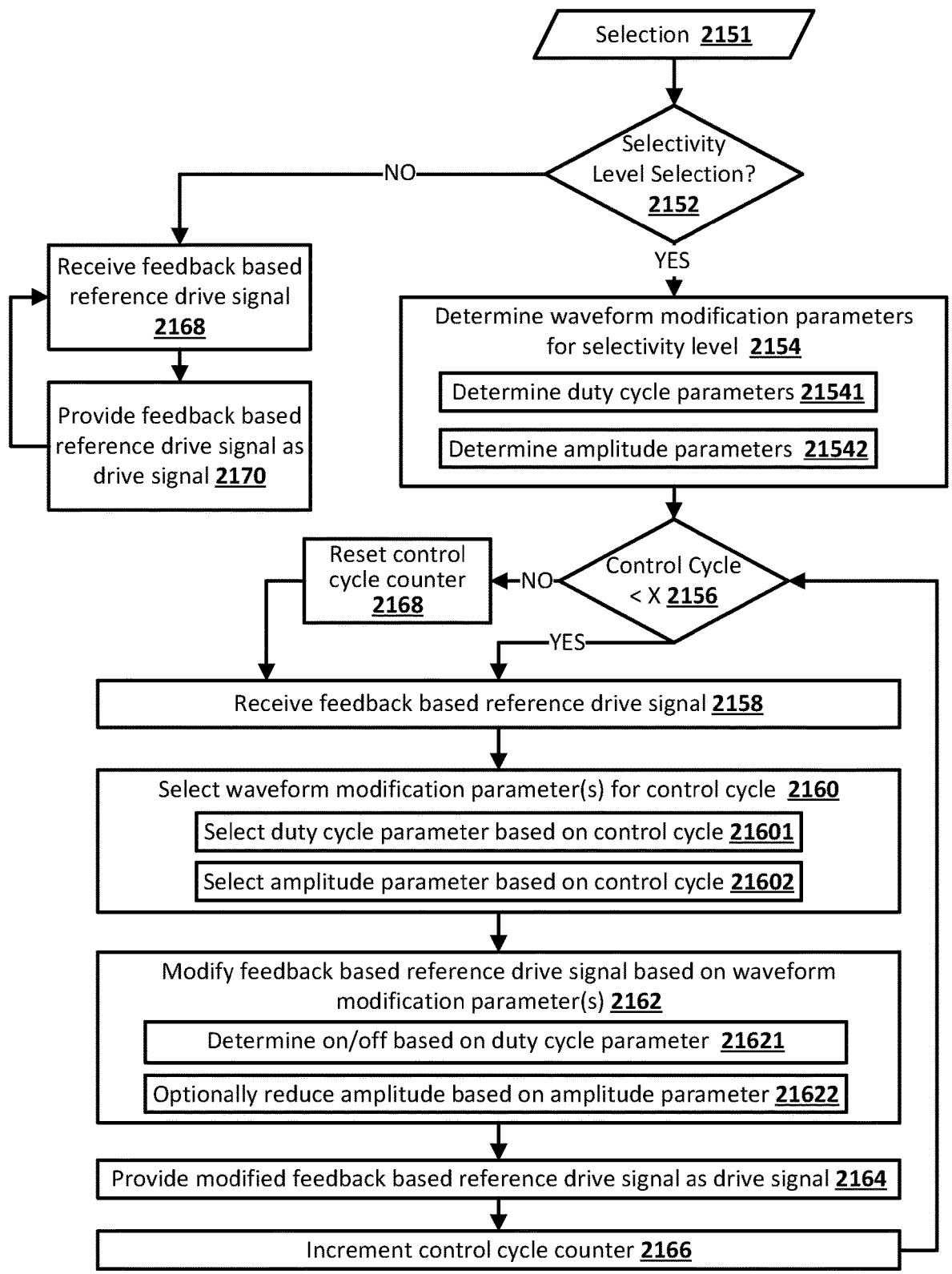
FIG. 21 illustrates an example method in accordance with various implementations.

FIG. 21 illustrates an example method according to various implementations disclosed herein. The example method can be performed by one or more controllers, such as one or more controllers of FIG. 17. Other implementations may perform the steps of FIG. 21 in a different order, omit certain steps, and/or perform different and/or additional steps than those illustrated in FIG. 21.

In FIG. 21, a selection 2151 is received and it is determined, at block 2151, whether the selection 2151 is a selectivity level selection. The selection 2151 can be a selection received in response to user interface input provided by a surgeon, such as user interface input provided via a step pedal and/or other user interface.

If the selection is not a selectivity level selection (e.g., it is a selection of "no" selectivity), the controller proceeds to perform multiple iterations of blocks 2168 and 2170. At block 2168, the controller receives a feedback based reference drive signal. The feedback based reference drive signal can be generated based on output from a sense ceramic as described herein. For example, the feedback based reference drive signal can be generated in view of the output from the sense ceramic and in an attempt to maintain driving of drive ceramics at a resonant frequency and/or in an attempt to maintain desired tip deflection. At block 2170 the controller provides the feedback based reference drive signal as a drive signal for driving one or more drive ceramics of an ultrasonic transducer. The system may then proceed back to block 2168 and receive the feedback based reference drive signal as further adapted based on further output from the sense ceramic. This loop can continue until, for example, a new selection occurs that is a selectivity level selection or until another stop condition is encountered (e.g., an explicit "stop" user interface input).

If the selection 2151 (or a subsequent selection) is a selectivity selection, at block 2151 the controller determines such selectivity selection, and proceeds to block 2154. At block 2154, the controller determines waveform modification parameters for the selectivity level of the selection. As described herein, multiple selectivity levels can be available, and the waveform modification parameters for the various selectivity levels can each vary relative to one another. As also described herein, the waveform modification parameters are stored in association with the selectivity level. For example, the parameters can be stored in a lookup table in association with the selectivity level.

Block 2154 can include sub-block 21541 and sub-block 21542. At sub-block 21541 the controller determines duty cycle parameters for the selectivity level. The duty cycle parameters can define, for example, a length of a duty cycle for the selectivity level and/or on and off durations for the duty cycle for the selectivity level. As sub-block 21542 the controller determines amplitude parameters. The amplitude parameters can define how an amplitude of a drive signal should be modulated throughout time for the selectivity level. For example, the amplitude parameters can include a sequence of discrete values, where each of the discrete values defines how amplitude of a feedback based reference signal should be modified during one or more control cycles of the duty cycle.

At block 2156, the controller determines if a control cycle counter is less than "X", where "X" can be based on the duty cycle duration. At an initial iteration of block 2156 for a selectivity level, the control cycle counter can be "0". If the control cycle counter is less than "X", the system proceeds to block 2158 and the controller receives the feedback based reference drive signal. The system then proceeds to block 2160 and selects waveform modification parameter(s), of the parameters determined at block 2154, for the control cycle. Block 2160 can include sub-blocks 21601 and 21602. At block 21601 the system selects a duty cycle parameter based on the control cycle. For example, the system can select either an "on" or "off" value based on the selected value corresponding to the current control cycle. At block 21602, the system selects an amplitude parameter based on the control cycle. For example, the system can select an amplitude parameter that corresponds to the current control cycle.

At block 2162, the controller modifies the feedback based reference drive signal based on the waveform modification parameter(s) selected at block 2160. Block 2162 can include sub-blocks 21621 and 21622. At sub-block 21621 the system determines whether the drive signal is on or off based on the duty cycle parameter selected at block 21601. At sub-block 21622, the system optionally (i.e., if the drive signal is "on") reduces an amplitude of the feedback based reference drive signal based on the amplitude parameter selected at block 21622. For example, the system can reduce the amplitude by a percentage dictated by the amplitude parameter.

At block 2164, the system provides the modified feedback based reference drive signal, as a drive signal, to one or more driving transducers.

At block 2166, the controller increments the control cycle counter. The system then proceeds back to block 2156 and, if the control cycle counter is less than "X", the controller then performs another iteration of blocks 2158, 2160, 2162, 2164, and 2166. It is noted that in one or more subsequent iteration(s) of block 2160, different amplitude parameter(s) will be selected, thereby providing different extents of modification at various control cycles. When, at block 2156, it is determined the control cycle counter is not less than "X", the controller can proceed to block 2168, reset the control counter, then proceed to block 2158. By resetting the control counter the controller will again cycle through the duty cycle parameters and/or amplitude parameters of the selected selectivity level over another duty cycle.

This general process can continue until, for example, a new selection input is received. If the new selection input is another selectivity level selection, for another selectivity level, multiple iterations of blocks 2154 through 2166 can be performed, utilizing waveform modification parameters that are specific to the another selectivity level.

Example. User Testing of Dissection with Tissue Selectivity

Finer dissection with high selectivity of the new transducer and control systems, where the surgeon could finely clean a large vessel of all tissue. This was accomplished at user testing. The actual surgery would progress faster than this with a bleeding liver, but the demonstration shows the capability exceeded the range of selectivity needed by the surgeon.

High speed digital imaging from 1000 frames per second to 150,000 frames per second was accomplished of vessels in bovine liver. With tissue selectivity active, the vessels were simply preserved longer under similar traction or loading. Finer vessels that would commonly be sealed could be preserved while removing the matrix liver material.

The vessel can be crossed with the ultrasonic aspirating or dwelled on for a period of time. In some instances, frothing, bubbling, and emulsification within the saline or adjacent tissue are observed just before the vessel is taken.

The vessel is crossed and frothing, bubbling, and emulsification are observed leading to severing of the vessel. This indication of cavitation is also apparent within the flue, once it occurs. It may be saline reaching the surgical tip enables cavitation of tissue that is more viscoelastic, or that onset is a result of adjacent tissue.

In very high speed imaging, such as 150,000 frames per second, the vessel is observed not to follow the retracting annulus of the surgical tip. Preservation of the vessel could be enhanced due to the negative half cycle being necessary to cavitation. Bubbles are compressed in the positive half cycle, but may break in the negative half cycle, given a great enough amplitude and period of time to expand to critical.

In a portion of the user testing, surgeons experimented with different tissue selectivity settings in a goat brain model. The common application is glioma tumor removal. The surgeons could selectively take brain matter while preserving the next pia, fine vessels, and gyrus. Additionally, we had observed the capability of taking softer gray matter, selectively leaving white matter. At least on surgeon noticed he could differentiate gray and white, and commented that he could not do this with earlier systems.

In our work, the white matter became resistant to removal with tissue selectivity at low amplitudes; for example, a 10% amplitude setting (about 18 micrometers peak-peak) and a tissue selectivity setting of medium, 3, or high, 4, took gray matter but the white mater became tacky, like the elasticity of "Silly putty", and remained even when going across the tissue many times.

The invention may be embodied in other forms without departure from the scope and essential characteristics thereof. The implementations described therefore are to be considered in all respects as illustrative and not restrictive. Although the present invention has been described in terms of certain preferred implementations, other implementations that are apparent to those of ordinary skill in the art are also within the scope of the invention.

The invention claimed is:

1. A method of modulating amplitude of a drive signal applied to at least one transducer of an ultrasonic surgical apparatus, the method comprising:
   identifying a selection of a particular tissue selectivity level, the particular tissue selectivity level being one of a plurality of available tissue selectivity levels;
   determining particular waveform modification parameters for the particular tissue selectivity level, wherein the particular waveform modification parameters are particularized to the particular tissue selectivity level and are determined based on being stored, in one or more computer readable media, in association with the particular tissue selectivity level;
   in response to the selection of the particular tissue selectivity level and until occurrence of a stop condition:
      generating the drive signal based on the particular waveform modification parameters, wherein generating the drive signal based on the particular waveform modification parameters comprises:
         selectively modifying a feedback based reference drive signal based on the particular waveform modification parameters to generate the drive signal with an amplitude that is modulated based on the particular waveform modification parameters that are stored in association with the particular tissue selectivity level.

2. The method of claim 1, wherein the particular waveform modification parameters comprise three or more discrete values each indicating an extent by which to reduce a reference amplitude of the feedback based reference signal in modifying the feedback based reference drive signal to generate the drive signal with the amplitude that is modulated.

3. The method of claim 2, wherein selectively modifying the feedback based reference drive signal based on the particular waveform modification parameters comprises:
   at a first control cycle, reducing the reference amplitude of the feedback based reference drive signal by a first extent that is based on a first discrete value of the three or more discrete values,
   at a second control cycle, reducing the reference amplitude of the feedback based reference drive signal by a second extent that is based on a second discrete value of the three or more discrete values, and
   at a third control cycle, reducing the reference amplitude of the feedback based reference drive signal by a third extent that is based on the third discrete value of the three of more discrete values.

4. The method of claim 3, wherein the second control cycle immediately follows the first control cycle.

5. The method of claim 3, wherein one or more intermediate control cycles are interposed between the first control cycle and the second control cycle, and wherein modifying the feedback based reference drive signal based on the particular waveform modification parameters further comprises:
   at each of the intermediary control cycles, reducing the reference amplitude of the feedback based reference drive signal by the first extent that is based on the first discrete value of the three or more discrete values.

6. The method of claim 3, wherein selectively modifying the feedback based reference drive signal based on the particular waveform modification parameters further comprises:
   at a fourth control cycle, maintaining the reference amplitude of the feedback based reference drive signal based on a fourth discrete value of the three or more discrete values.

7. The method of claim 2, wherein the three or more discrete values are stored with an indication of a sequence of the three or more discrete values, and wherein selectively modifying the feedback based reference drive signal based on the particular waveform modification parameters to generate the drive signal with the amplitude that is modulated based on the particular waveform modification parameters comprises:
   at one or more first control cycles, reducing the reference amplitude of the feedback based reference drive signal by a first extent that is based on a first discrete value of the three or more discrete values,
   at one or more second control cycles that immediately follow the one or more first control cycles, reducing the reference amplitude of the feedback based reference drive signal by a second extent that is based on a second discrete value of the three or more discrete values, wherein the second discrete value is utilized at the one or more second control cycles based on the second discrete value following the first discrete value in the sequence, and based on the one or more second control cycles immediately following the one or more first control cycles.

8. The method of claim 1, wherein the waveform modification parameters define a particular duty cycle that is particularized to the particular tissue selectivity level, and wherein the waveform modification parameters further define three or more values that are each utilized to determine the amplitude at a corresponding segment of the duty cycle.

9. The method of claim 1, wherein the waveform modification parameters comprise twenty or more sequential discrete values, and wherein selectively modifying the feedback based reference drive signal based on the particular waveform modification parameters comprises cycling through the sequential discrete values in sequence to selectively modify, at each of a plurality of control cycles, the feedback based reference drive signal based on a corresponding one of the sequential discrete values.

10. The method of claim 1, wherein the waveform modification parameters are stored in a look-up table in the one or more computer readable media.

11. The method of claim 1, wherein the one or more computer readable media comprises non-volatile memory.

12. The method of claim 1, wherein identifying the selection of the particular tissue selectivity level is based on user interface input received in response to interaction of a surgeon with one or more user interface input devices.

13. The method of claim 12, wherein the one or more user interface input devices comprise a foot pedal.

14. The method of claim 12, wherein the stop condition comprises identifying a selection of an additional tissue selectivity level of the plurality of available tissue selectivity levels, and further comprising:
   identifying the selection of the additional tissue selectivity level;
   determining additional waveform modification parameters for the additional tissue selectivity level, wherein the additional waveform modification parameters differ from the particular waveform modification parameters, and wherein the additional waveform modification parameters are determined based on being stored, in one or more of the computer readable media, in association with the additional tissue selectivity level;

in response to the selection of the additional tissue selectivity level and until occurrence of another stop condition:

generating the drive signal based on the additional waveform modification parameters, wherein generating the drive signal based on the additional waveform modification parameters comprises:

selectively modifying the feedback based reference drive signal based on the additional waveform modification parameters to generate the drive signal with the amplitude being modulated based on the additional waveform modification parameters that are stored in association with the additional tissue selectivity level.

15. The method of claim 1, wherein the stop condition comprises a stop command that is based on user interface input received in response to interaction of a surgeon with one or more user interface input devices.

16. The method of claim 1, further comprising:

generating the feedback based reference drive signal based on sense electrical output received from a sense ceramic mechanically coupled with the at least one transducer.

* * * * *